(12) United States Patent
Kim et al.

(10) Patent No.: US 9,597,378 B2
(45) Date of Patent: Mar. 21, 2017

(54) BLOOD COAGULATION FACTOR VII AND VIIA DERIVATIVES, CONJUGATES AND COMPLEXES COMPRISING THE SAME, AND USE THEREOF

(71) Applicant: HANMI SCIENCE CO., LTD., Hwaseong-si, Gyeonggi-do (KR)

(72) Inventors: Dae Jin Kim, Hwaseong-si (KR); Byung Sun Lee, Seoul (KR); Sung Hwan Hong, Seoul (KR); Yong Ho Huh, Seoul (KR); Sung Youb Jung, Suwon-si (KR); Se Chang Kwon, Seoul (KR)

(73) Assignee: HANMI SCIENCE CO., LTD., Hwaseong-shi (KR)

( * ) Notice: Subject to any disclaimer, the term of this patent is extended or adjusted under 35 U.S.C. 154(b) by 0 days.

(21) Appl. No.: 14/349,925

(22) PCT Filed: Oct. 5, 2012

(86) PCT No.: PCT/KR2012/008102
§ 371 (c)(1),
(2) Date: Apr. 4, 2014

(87) PCT Pub. No.: WO2013/051900
PCT Pub. Date: Apr. 11, 2013

(65) Prior Publication Data
US 2014/0271607 A1    Sep. 18, 2014

(30) Foreign Application Priority Data

Oct. 6, 2011 (KR) .................. 10-2011-0102099

(51) Int. Cl.
| | |
|---|---|
| *A61K 38/36* | (2006.01) |
| *A61K 38/16* | (2006.01) |
| *A61K 48/00* | (2006.01) |
| *A61P 7/04* | (2006.01) |
| *A61K 38/48* | (2006.01) |
| *C12N 9/64* | (2006.01) |
| *A61K 47/48* | (2006.01) |

(52) U.S. Cl.
CPC ...... *A61K 38/4846* (2013.01); *A61K 47/4843* (2013.01); *C12N 9/6437* (2013.01); *A61K 48/00* (2013.01); *C07K 2319/30* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 7,432,352 B2 | 10/2008 | Johansen | |
| 2003/0044908 A1 | 3/2003 | Persson | |
| 2006/0258851 A1 | 11/2006 | Johansen | |
| 2006/0269553 A1 | 11/2006 | Kim et al. | |
| 2008/0260755 A1 | 10/2008 | Metzner | |
| 2009/0041744 A1* | 2/2009 | Ostergaard et al. | 424/94.6 |
| 2009/0298760 A1 | 12/2009 | Weimer et al. | |
| 2010/0317585 A1 | 12/2010 | Fima et al. | |

FOREIGN PATENT DOCUMENTS

| | | |
|---|---|---|
| CN | 1723219 A | 1/2006 |
| EP | 2361932 A1 | 8/2011 |
| JP | 2007-509843 A | 4/2007 |
| JP | 2009-539391 A | 11/2009 |
| RU | 2 338 752 C2 | 11/2008 |
| RU | 2 356 909 C2 | 5/2009 |
| WO | 02/077218 A1 | 10/2002 |
| WO | 2004006962 A2 | 1/2004 |
| WO | 2005/047334 A1 | 5/2005 |
| WO | 2007/144173 A1 | 12/2007 |
| WO | 2011/004361 A2 | 1/2011 |

OTHER PUBLICATIONS

Schellenberger et al., "A recombinant polypeptide extends the in vivo half-life of peptides and proteins in a tunable manner," Nat. Biotech. 27:1186-1190 (2009) (26 pages in total, including supplementary info).*

UniProt Accession No. P08709, coagulation factor VII (last modified Jan. 1, 1988), accessed at uniprot.org/uniprot/P08709 on Jun. 7, 2015.*

Stevens et al., "Modification of Superoxide Dismutase 1 (SOD1) Properties by a GFP Tag—Implications for Research into Amyotrophic Lateral Sclerosis (ALS)," PLOSone 5(3):e9541 (2010), pp. 1-10.*

UniProt Accession No. Q6YGZO, green fluorescent protein (last modified Jul. 5, 2004), accessed at uniprot.org/uniprot/Q6YGZO on Jun. 7, 2015.*

(Continued)

Primary Examiner — Julie Ha
Assistant Examiner — Kristina M Hellman
(74) Attorney, Agent, or Firm — Sughrue Mion, PLLC

(57) ABSTRACT

A blood coagulation factor VII derivative, a blood coagulation factor VIIa derivative, FacVII and FacVIIa conjugates are prepared by linking a polymer capable of extending the blood half-life to the derivative. FacVII and VIIa complexes each prepared by linking a carrier to the conjugate, genes encoding the FacVII and FacVIIa derivatives, expression vectors comprising the genes, transformants introduced with the expression vectors, a method for preparing the FacVII and FacVIIa derivatives using the transformants, a method for preparing the FacVIIa conjugate and complex, a FacVIIa complex prepared by the method, a pharmaceutical composition for the prevention or treatment of hemophilia comprising the derivative, conjugate, or complex as an active ingredient, and a pharmaceutical composition for blood coagulation comprising the derivative, conjugate, or complex as an active ingredient are described.

27 Claims, 4 Drawing Sheets

(56) References Cited

OTHER PUBLICATIONS

International Searching Authority, International Search Report of PCT/KR2012/008102 Dated Mar. 28, 2013.
New Zealand Intellectual Property Office; Communication dated Feb. 3, 2015 in counterpart Application No. 623726, pp. 1-3.
European Patent Office; Communication dated Jun. 30, 2015 in counterpart Application No. 12838228.0, pp. 1-6.
State Intellectual Property Office of the People's Republic of China; Communication dated Mar. 6, 2015 in counterpart Application No. 201280060378.X, pp. 1-9.
Japanese Patent Office; Communication dated Jul. 27, 2016 in counterpart application No. 2014-534483.
Russian Patent Office; Communication dated Jul. 11, 2016 in counterpart application No. 2014115291/10(023876).

\* cited by examiner

SEQUENCE LISTING

<160> NUMBER OF SEQ ID NOS: 37

<210> SEQ ID NO 1
<211> LENGTH: 34
<212> TYPE: DNA
<213> ORGANISM: Artificial Sequence
<220> FEATURE:
<223> OTHER INFORMATION: Synthetic VIIBHISS F

<400> SEQUENCE: 1
cccggatcca tggtctccca ggccctcagg ctcc                                34

<210> SEQ ID NO 2
<211> LENGTH: 31
<212> TYPE: DNA
<213> ORGANISM: Artificial Sequence
<220> FEATURE:
<223> OTHER INFORMATION: Synthetic VIIXhoIAS R

<400> SEQUENCE: 2
gggctcgagc tagggaaatg gggctcgcag g                                  31

<210> SEQ ID NO 3
<211> LENGTH: 1335
<212> TYPE: DNA
<213> ORGANISM: Artificial Sequence
<220> FEATURE:
<223> OTHER INFORMATION: Synthetic FactorVII DNA

<400> SEQUENCE: 3
atggtctccc aggccctcag gctcctctgc cttctgcttg gcttcagggg ctgcctggct    60
gcagtcttcg taacccagga ggaagcccac ggcgtcctgc accggcgccg cgcgccaac   120 gcgttcctgg aggagctgcg gccgggctcc ctggagaggg agtgcaagga ggagcagtgc   180
tccttcgagg aggcccggga gatcttcaag gacgcggaga ggacgaagct gttctggatt   240
tcttacagtg atggggacca gtgtgcctca gtccatgcc agaatggggg ctcctgcaag   300
gaccagctcc agtcctatat ctgcttctgc ctccctgcct cgagggccg gaactgtgag   360 acgcacaagg atgaccagct gatctgtgtg aacgagaacg gcggctgtga gcagtactgc   420
agtgaccaca cgggcaccaa gcgctcctgt cggtgccacg agggtactc tctgctggca   480 gacgggggtg cctgcacacc cacagttgaa tatccatgtg aaaaatacc tattctagaa   540 aaaagaaatg ccagcaaacc caaggccga attgtggggg caaggtgtg ccccaaaggg   600 gagtgtccat ggcaggtcct gttgttggtg aatggagctc agttgtgtgg ggggaccctg   660
atcaacacca tctgggtggt ctccgcggcc cactgtttcg acaaaatcaa gaactggagg   720
aacctgatcg cggtgctggg cgagcacgac ctcagcgagc acgacgggga tgagcagagc   780
cggcgggtgg cgcaggtcat catccccagc acgtacgtcc cggcaccac caaccacgac   840 atcgcgctgc tccgcctgca ccagcccgtg gtcctcactg accatgtggt gcccctctgc   900
ctgcccgaac ggacgttctc tgagaggacg ctggccttcg tgcgcttctc attggtcagc   960
ggctggggcc agctgctgga ccgtggcgcc acggccctgg agctcatggt cctcaacgtg  1020
ccccggctga tgacccagga ctgcctgcag cagtcacgga aggtgggaga ctccccaaat  1080
atcacggagt acatgttctg tgccggctac tcggatggca gcaaggactc ctgcaagggg  1140
gacagtggag cccacatgc cacccactac cggggcacgt ggtacctgac gggcatcgtc  1200
agctggggcc agggctgcgc aaccgtgggc cactttgggg tgtacaccag ggtctcccag  1260
tacatcgagt ggctgcaaaa gctcatgcgc tcagagccac gcccaggagt cctcctgcga  1320
gccccatttc cctag 1335

<210> SEQ ID NO 4
<211> LENGTH: 444
<212> TYPE: PRT
<213> ORGANISM: Artificial Sequence
<220> FEATURE:
<223> OTHER INFORMATION: Synthetic FactorVII

<400> SEQUENCE: 4

```
Met Val Ser Gln Ala Leu Arg Leu Leu Cys Leu Leu Leu Gly Leu Gln
 1               5                  10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350
```

```
Arg Lys Val Gly Asp Ser Pro Asn Ile Thr Glu Tyr Met Phe Cys Ala
                355                 360                 365

Gly Tyr Ser Asp Gly Ser Lys Asp Ser Cys Lys Gly Asp Ser Gly Gly
        370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro
            435                 440

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide-SOD1 1-6

<400> SEQUENCE: 5

Ala Thr Lys Ala Val Cys
  1               5

<210> SEQ ID NO 6
<211> LENGTH: 45
<212> TYPE: DNA
<213> ORGANISM: Artificial Sequence
<220> FEATURE:
<223> OTHER INFORMATION: FVIIEcoRISS F

<400> SEQUENCE: 6
ccggaattca tggccaacgc gttcctggag gagctgcggc cgggc                45

<210> SEQ ID NO 7
<211> LENGTH: 62
<212> TYPE: DNA
<213> ORGANISM: Artificial Sequence
<220> FEATURE:
<223> OTHER INFORMATION: Synthetic FVII#1XhoIAS R

<400> SEQUENCE: 7
ccgctcgagt cagcacacgg ccttcgtcgc gggaaatggg gctcgcagga ggactcctgg    60
gc                                                                  62

<210> SEQ ID NO 8
<211> LENGTH: 1353
<212> TYPE: DNA
<213> ORGANISM: Artificial Sequence
<220> FEATURE:
<223> OTHER INFORMATION: Synthetic FactorVII-ATKAVC DNA

<400> SEQUENCE: 8
atggtctccc aggccctcag gctcctctgc cttctgcttg gcttcagggg ctgcctggct    60
gcagtcttcg taacccagga ggaagcccac ggcgtcctgc accggcgccg gcgcgccaac   120
gcgttcctgg aggagctgcg gccgggctcc ctggagaggg agtgcaagga ggagcagtgc   180
tccttcgagg aggcccggga gatcttcaag gacgcggaga ggacgaagct gttctggatt   240
tcttacagtg atggggacca gtgtgcctca gtccatgcc agaatggggg ctcctgcaag   300
gaccagctcc agtcctatat ctgcttctgc ctccctgcct cgagggccg gaactgtgag   360
```

```
acgcacaagg atgaccagct gatctgtgtg aacgagaacg gcggctgtga gcagtactgc      420
agtgaccaca cgggcaccaa gcgctcctgt cggtgccacg aggggtactc tctgctggca      480
gacggggtgt cctgcacacc cacagttgaa tatccatgtg aaaaatacc tattctagaa       540 aaaagaaatg ccagcaaacc ccaaggccga attgtggggg caaggtgtg ccccaaaggg       600 gagtgtccat ggcaggtcct gttgttggtg aatggagctc agttgtgtgg ggggaccctg      660
atcaacacca tctgggtggt ctccgcggcc cactgtttcg acaaaatcaa gaactggagg      720
aacctgatcg cggtgctggg cgagcacgac ctcagcgagc acgacgggga tgagcagagc      780
cggcgggtgg cgcaggtcat catccccagc acgtacgtcc cgggcaccac caaccacgac      840
atcgcgctgc tccgcctgca ccagcccgtg gtcctcactg accatgtggt gcccctctgc      900
ctgcccgaac ggacgttctc tgagaggacg ctggccttcg tgcgcttctc attggtcagc      960
ggctggggcc agctgctgga ccgtggcgcc acggccctgg agctcatggt cctcaacgtg     1020
ccccggctga tgacccagga ctgcctgcag cagtcacgga aggtgggaga ctcccccaaat    1080 atcacggagt acatgttctg tgccggctac tcggatggca gcaaggactc ctgcaagggg     1140
gacagtggag gcccacatgc cacccactac cggggcacgt ggtacctgac gggcatcgtc     1200
agctggggcc agggctgcgc aaccgtgggc cactttgggg tgtacaccag ggtctcccag     1260
tacatcgagt ggctgcaaaa gctcatgcgc tcagagccac gcccaggagt cctcctgcga     1320
gccccatttc ccgcgacgaa ggccgtgtgc tga                                  1353

<210> SEQ ID NO 9
<211> LENGTH: 450
<212> TYPE: PRT
<213> ORGANISM: Artificial Sequence
<220> FEATURE:
<223> OTHER INFORMATION: Synthetic FactorVII-ATKAVC

<400> SEQUENCE: 9

Gly Gly Lys Val Cys Pro Lys Gly Glu Cys Pro Trp Gln Val Leu Leu
            195                 200                 205
Leu Val Asn Gly Ala Gln Leu Cys Gly Gly Thr Leu Ile Asn Thr Ile
    210                 215                 220
Trp Val Val Ser Ala Ala His Cys Phe Asp Lys Ile Lys Asn Trp Arg
225                 230                 235                 240
Asn Leu Ile Ala Val Leu Gly Glu His Asp Leu Ser Glu His Asp Gly
                245                 250                 255
Asp Glu Gln Ser Arg Arg Val Ala Gln Val Ile Ile Pro Ser Thr Tyr
            260                 265                 270
Val Pro Gly Thr Thr Asn His Asp Ile Ala Leu Leu Arg Leu His Gln
        275                 280                 285
Pro Val Val Leu Thr Asp His Val Val Pro Leu Cys Leu Pro Glu Arg
    290                 295                 300
Thr Phe Ser Glu Arg Thr Leu Ala Phe Val Arg Phe Ser Leu Val Ser
305                 310                 315                 320
Gly Trp Gly Gln Leu Leu Asp Arg Gly Ala Thr Ala Leu Glu Leu Met
                325                 330                 335
Val Leu Asn Val Pro Arg Leu Met Thr Gln Asp Cys Leu Gln Gln Ser
            340                 345                 350
Arg Lys Val Gly Asp Ser Pro Asn Ile Thr Glu Tyr Met Phe Cys Ala
        355                 360                 365
Gly Tyr Ser Asp Gly Ser Lys Asp Ser Cys Lys Gly Asp Ser Gly Gly
    370                 375                 380
Pro His Ala Thr His Tyr Arg Gly Thr Trp Tyr Leu Thr Gly Ile Val
385                 390                 395                 400
Ser Trp Gly Gln Gly Cys Ala Thr Val Gly His Phe Gly Val Tyr Thr
                405                 410                 415
Arg Val Ser Gln Tyr Ile Glu Trp Leu Gln Lys Leu Met Arg Ser Glu
            420                 425                 430
Pro Arg Pro Gly Val Leu Leu Arg Ala Pro Phe Pro Ala Thr Lys Ala
        435                 440                 445
Val Cys
    450

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Gly Gly Gly Gly Ser Cys
  1               5

<210> SEQ ID NO 11
<211> LENGTH: 62
<212> TYPE: DNA
<213> ORGANISM: Artificial Sequence
<220> FEATURE:
<223> OTHER INFORMATION: Synthetic FVII#2XhoIAS R

<400> SEQUENCE: 11
ccgctcgagt cagcaggagc cgccgccgcc gggaaatggg gctcgcagga ggactcctgg      60
gc                                                                    62

<210> SEQ ID NO 12
<211> LENGTH: 1353
<212> TYPE: DNA
<213> ORGANISM: Artificial Sequence
<220> FEATURE:
<223> OTHER INFORMATION: FactorVII-GGGGSC DNA

<400> SEQUENCE: 12

```
atggtctccc aggccctcag gctcctctgc cttctgcttg gcttcagggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atgggaccca gtgtgcctca agtccatgcc agaatggggg ctcctgcaag     300
gaccagctcc agtcctatat ctgcttctgc ctccctgcct tcgagggccg aactgtgag     360
acgcacaagg atgaccagct gatctgtgtg aacgagaacg gcggctgtga gcagtactgc     420
agtgaccaca cgggcaccaa gcgctcctgt cggtgccacg aggggtactc tctgctggca     480
gacggggtgt cctgcacacc cacagttgaa tatccatgtg gaaaaatacc tattctagaa     540
aaaagaaatg ccagcaaacc ccaaggccga attgtggggg caaggtgtg ccccaaaggg     600
gagtgtccat ggcaggtcct gttgttggtg aatggagctc agttgtgtgg ggggaccctg     660
atcaacacca tctgggtggt ctccgcggcc cactgtttcg acaaaatcaa gaactggagg     720
aacctgatcg cggtgctggg cgagcacgac ctcagcgagc acgacgggga tgagcagagc     780
cggcgggtgg cgcaggtcat catccccagc acgtacgtcc cggcaccac caaccacgac     840
atcgcgctgc tccgcctgca ccagcccgtg gtcctcactg accatgtggt gcccctctgc     900
ctgcccgaac ggacgttctc tgagaggacg ctggccttcg tgcgcttctc attggtcagc     960
ggctggggcc agctgctgga ccgtggcgcc acggccctgg agctcatggt cctcaacgtg    1020
ccccggctga tgacccagga ctgcctgcag cagtcacgga aggtgggaga ctccccaaat    1080
atcacggagt acatgttctg tgccggctac tcggatggca gcaaggactc ctgcaagggg    1140
gacagtggag cccacatgc cacccactac cggggcacgt ggtacctgac gggcatcgtc    1200
agctggggcc agggctgcgc aaccgtgggc cactttgggg tgtacaccag gtctcccag    1260
tacatcgagt ggctgcaaaa gctcatgcgc tcagagccac gcccaggagt cctcctgcga    1320
gccccatttc ccggcggcgg cggctcctgc tga                                1353
```

<210> SEQ ID NO 13
<211> LENGTH: 450
<212> TYPE: PRT
<213> ORGANISM: Artificial Sequence
<220> FEATURE:
<223> OTHER INFORMATION: Synthetic FactorVII-GGGGSC

<400> SEQUENCE: 13

Met Val Ser Gln Ala Leu Arg Leu Leu Cys Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile

```
            65                  70                  75                  80
        Ser Tyr Ser Asp Gly Asp Gln Cys Ala Ser Ser Pro Cys Gln Asn Gly
                        85                  90                  95

Gly Ser Cys Lys Asp Gln Leu Gln Ser Tyr Ile Cys Phe Cys Leu Pro
                    100                 105                 110

Ala Phe Glu Gly Arg Asn Cys Glu Thr His Lys Asp Asp Gln Leu Ile
                    115                 120                 125

Cys Val Asn Glu Asn Gly Gly Cys Glu Gln Tyr Cys Ser Asp His Thr
                130                 135                 140

Gly Thr Lys Arg Ser Cys Arg Cys His Glu Gly Tyr Ser Leu Leu Ala
        145                 150                 155                 160

Asp Gly Val Ser Cys Thr Pro Thr Val Glu Tyr Pro Cys Gly Lys Ile
                        165                 170                 175

Pro Ile Leu Glu Lys Arg Asn Ala Ser Lys Pro Gln Gly Arg Ile Val
                    180                 185                 190

Gly Gly Lys Val Cys Pro Lys Gly Glu Cys Pro Trp Gln Val Leu Leu
                    195                 200                 205

Leu Val Asn Gly Ala Gln Leu Cys Gly Gly Thr Leu Ile Asn Thr Ile
                    210                 215                 220

Trp Val Val Ser Ala Ala His Cys Phe Asp Lys Ile Lys Asn Trp Arg
        225                 230                 235                 240

Asn Leu Ile Ala Val Leu Gly Glu His Asp Leu Ser Glu His Asp Gly
                        245                 250                 255

Asp Glu Gln Ser Arg Arg Val Ala Gln Val Ile Ile Pro Ser Thr Tyr
                    260                 265                 270

Val Pro Gly Thr Thr Asn His Asp Ile Ala Leu Leu Arg Leu His Gln
                    275                 280                 285

Pro Val Val Leu Thr Asp His Val Val Pro Leu Cys Leu Pro Glu Arg
                    290                 295                 300

Thr Phe Ser Glu Arg Thr Leu Ala Phe Val Arg Phe Ser Leu Val Ser
        305                 310                 315                 320

Gly Trp Gly Gln Leu Leu Asp Arg Gly Ala Thr Ala Leu Glu Leu Met
                        325                 330                 335

Val Leu Asn Val Pro Arg Leu Met Thr Gln Asp Cys Leu Gln Gln Ser
                    340                 345                 350

Arg Lys Val Gly Asp Ser Pro Asn Ile Thr Glu Tyr Met Phe Cys Ala
                    355                 360                 365

Gly Tyr Ser Asp Gly Ser Lys Asp Ser Cys Lys Gly Asp Ser Gly Gly
                    370                 375                 380

Pro His Ala Thr His Tyr Arg Gly Thr Trp Tyr Leu Thr Gly Ile Val
        385                 390                 395                 400

Ser Trp Gly Gln Gly Cys Ala Thr Val Gly His Phe Gly Val Tyr Thr
                        405                 410                 415

Arg Val Ser Gln Tyr Ile Glu Trp Leu Gln Lys Leu Met Arg Ser Glu
                    420                 425                 430

Pro Arg Pro Gly Val Leu Leu Arg Ala Pro Phe Pro Gly Gly Gly Gly
                    435                 440                 445

Ser Cys
            450

<210> SEQ ID NO 14
<211> LENGTH: 593
<212> TYPE: PRT
<213> ORGANISM: Artificial Sequence
```

```
<220> FEATURE:
<223> OTHER INFORMATION: Synthetic FactorVII-SOD1 1~149

<400> SEQUENCE: 14

Met Val Ser Gln Ala Leu Arg Leu Leu Cys Leu Leu Leu Gly Leu Gln
 1               5                  10                  15

Gly Cys Leu Ala Ala Val Phe Val Thr Gln Glu Glu Ala His Gly Val
             20                  25                  30

Leu His Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
     50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400
```

```
Ser Trp Gly Gln Gly Cys Ala Thr Val Gly His Phe Gly Val Tyr Thr
                405                 410                 415
Arg Val Ser Gln Tyr Ile Glu Trp Leu Gln Lys Leu Met Arg Ser Glu
            420                 425                 430
Pro Arg Pro Gly Val Leu Leu Arg Ala Pro Phe Pro Ala Thr Lys Ala
        435                 440                 445
Val Cys Val Leu Lys Gly Asp Gly Pro Val Gln Gly Ile Ile Asn Phe
    450                 455                 460
Glu Gln Lys Glu Ser Asn Gly Pro Val Lys Val Trp Gly Ser Ile Lys
465                 470                 475                 480
Gly Leu Thr Glu Gly Leu His Gly Phe His Val His Glu Phe Gly Asp
                485                 490                 495
Asn Thr Ala Gly Cys Thr Ser Ala Gly Pro His Phe Asn Pro Leu Ser
            500                 505                 510
Arg Lys His Gly Gly Pro Lys Asp Glu Glu Arg His Val Gly Asp Leu
        515                 520                 525
Gly Asn Val Thr Ala Asp Lys Asp Gly Val Ala Asp Val Ser Ile Glu
    530                 535                 540
Asp Ser Val Ile Ser Leu Ser Gly Asp His Cys Ile Ile Gly Arg Thr
545                 550                 555                 560
Leu Val Val His Glu Lys Ala Asp Asp Leu Gly Lys Gly Gly Asn Glu
                565                 570                 575
Glu Ser Thr Lys Thr Gly Asn Ala Gly Ser Arg Leu Ala Cys Gly Val
            580                 585                 590
Ile

<210> SEQ ID NO 15
<211> LENGTH: 1785
<212> TYPE: DNA
<213> ORGANISM: Artificial Sequence
<220> FEATURE:
<223> OTHER INFORMATION: Synthetic FactorVII-SOD1 1~149 DNA

<400> SEQUENCE: 15
atggtctccc aggccctcag gctcctctgc cttctgcttg gcttcagggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atggggacca gtgtgcctca gtccatgcc agaatggggg ctcctgcaag     300
gaccagctcc agtcctatat ctgcttctgc ctccctgcct tcgagggccg aactgtgag      360 acgcacaagg atgaccagct gatctgtgtg aacgagaacg gcggctgtga gcagtactgc     420
agtgaccaca cgggcaccaa gcgctcctgt cggtgccacg aggggtactc tctgctggca     480 gacgggtgt cctgcacacc cacagttgaa tatccatgtg aaaaatacc tattctagaa      540 aaaagaaatg ccagcaaacc ccaaggccga attgtggggg gcaaggtgtg ccccaaaggg     600
gagtgtccat ggcaggtcct gttgttggtg aatggagctc agttgtgtgg ggggaccctg     660
atcaacacca tctgggtggt ctccgcggcc cactgtttcg acaaaatcaa gaactggagg     720
aacctgatcg cggtgctggg cgagcacgac ctcagcgagc acgacgggga tgagcagagc     780
cggcgggtgg cgcaggtcat catccccagc acgtacgtcc cggcaccacc caaccacgac     840
atcgcgctgc tccgcctgca ccagcccgtg gtcctcactg accatgtggt gcccctctgc     900
```

```
ctgcccgaac ggacgttctc tgagaggacg ctggccttcg tgcgcttctc attggtcagc      960
ggctggggcc agctgctgga ccgtggcgcc acggccctgg agctcatggt cctcaacgtg     1020
ccccggctga tgacccagga ctgcctgcag cagtcacgga aggtgggaga ctccccaaat     1080
atcacggagt acatgttctg tgccggctac tcggatggca gcaaggactc ctgcaagggg     1140
gacagtggag gcccacatgc cacccactac cggggcacgt ggtacctgac gggcatcgtc     1200
agctggggcc agggctgcgc aaccgtgggc cactttgggg tgtacaccag gtctcccag     1260 tacatcgagt ggctgcaaaa gctcatgcgc tcagagccac gcccaggagt cctcctgcga     1320
gccccatttc ccgcgacgaa ggccgtgtgc gtgctgaagg gcgacggccc agtgcagggc     1380
atcatcaatt cgagcagaa ggaaagtaat ggaccagtga aggtgtgggg aagcattaaa      1440
ggactgactg aaggcctgca tggattccat gttcatgagt ttggagataa tacagcaggc     1500
tgtaccagtg caggtcctca ctttaatcct ctatccagaa acacggtgg gccaaaggat      1560 gaagagaggc atgttggaga cttgggcaat gtgactgctg acaaagatgg tgtggccgat     1620
gtgtctattg aagattctgt gatctcactc tcaggagacc attgcatcat tggccgcaca     1680
ctggtggtcc atgaaaaagc agatgacttg ggcaaggtg gaaatgaaga agtacaaag     1740 acaggaaacg ctggaagtcg tttggcttgt ggtgtaattg ggtga                     1785

<210> SEQ ID NO 16
<211> LENGTH: 34
<212> TYPE: DNA
<213> ORGANISM: Artificial Sequence
<220> FEATURE:
<223> OTHER INFORMATION: Synthetic FVIIEcoRISS F

<400> SEQUENCE: 16
ccggaattca tggtctccca ggccctcagg ctcc                                  34

<210> SEQ ID NO 17
<211> LENGTH: 34
<212> TYPE: DNA
<213> ORGANISM: Artificial Sequence
<220> FEATURE:
<223> OTHER INFORMATION: Synthetic FVIISOD1InfAS R

<400> SEQUENCE: 17
cggccttcgt cgcgggaaat ggggctcgca ggag                                  34

<210> SEQ ID NO 18
<211> LENGTH: 34
<212> TYPE: DNA
<213> ORGANISM: Artificial Sequence
<220> FEATURE:
<223> OTHER INFORMATION: Synthetic FVIISOD1InfSS F

<400> SEQUENCE: 18
gagccccatt tcccgcgacg aaggccgtgt gcgt                                  34

<210> SEQ ID NO 19
<211> LENGTH: 34
<212> TYPE: DNA
<213> ORGANISM: Artificial Sequence
<220> FEATURE:
<223> OTHER INFORMATION: Synthetic SOD1XhoIAS R

<400> SEQUENCE: 19
ccgctcgagt caaattacac cacaagccaa acga                                  34
```

<210> SEQ ID NO 20
<211> LENGTH: 593
<212> TYPE: PRT
<213> ORGANISM: Artificial Sequence
<220> FEATURE:
<223> OTHER INFORMATION: Synthetic FactorVII-SOD1 IPRI

<400> SEQUENCE: 20

```
Met Val Ser Gln Ala Leu Arg Leu Leu Cys Leu Leu Leu Gly Leu Gln
  1               5                  10                  15

Gly Cys Leu Ala Ala Val Phe Val Thr Gln Glu Glu Ala His Gly Val
             20                  25                  30

Leu His Arg Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
     50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
```

|  | 370 |  | 375 |  | 380 |  |  |  |
| --- |
Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ala Thr Lys Ala
        435                 440                 445

Val Cys Ile Pro Arg Ile Asp Gly Pro Val Gln Gly Ile Ile Asn Phe
    450                 455                 460

Glu Gln Lys Glu Ser Asn Gly Pro Val Lys Val Trp Gly Ser Ile Lys
465                 470                 475                 480

Gly Leu Thr Glu Gly Leu His Gly Phe His Val His Glu Phe Gly Asp
                485                 490                 495

Asn Thr Ala Gly Cys Thr Ser Ala Gly Pro His Phe Asn Pro Leu Ser
            500                 505                 510

Arg Lys His Gly Gly Pro Lys Asp Glu Glu Arg His Val Gly Asp Leu
        515                 520                 525

Gly Asn Val Thr Ala Asp Lys Asp Gly Val Ala Asp Val Ser Ile Glu
    530                 535                 540

Asp Ser Val Ile Ser Leu Ser Gly Asp His Cys Ile Ile Gly Arg Thr
545                 550                 555                 560

Leu Val Val His Glu Lys Ala Asp Asp Leu Gly Lys Gly Gly Asn Glu
                565                 570                 575

Glu Ser Thr Lys Thr Gly Asn Ala Gly Ser Arg Leu Ala Cys Gly Val
            580                 585                 590

Ile

<210> SEQ ID NO 21
<211> LENGTH: 1785
<212> TYPE: DNA
<213> ORGANISM: Artificial Sequence
<220> FEATURE:
<223> OTHER INFORMATION: Synthetic FactorVII-SOD1 IPRI DNA

<400> SEQUENCE: 21

| atggtctccc | aggccctcag | gctcctctgc | cttctgcttg | gcttcagggg | ctgcctggct | 60 |
| --- | --- | --- | --- | --- | --- | --- |
| gcagtcttcg | taacccagga | ggaagcccac | ggcgtcctgc | accggcgccg | gcgcgccaac | 120 |
| gcgttcctgg | aggagctgcg | gccgggctcc | ctggagaggg | agtgcaagga | ggagcagtgc | 180 |
| tccttcgagg | aggcccggga | gatcttcaag | gacgcggaga | ggacgaagct | gttctggatt | 240 |
| tcttacagtg | atgggggacca | gtgtgcctca | gtccatgcc | agaatgggg | ctcctgcaag | 300 |
| gaccagctcc | agtcctatat | ctgcttctgc | ctccctgcct | tcgagggccg | gaactgtgag | 360 |
| acgcacaagg | atgaccagct | gatctgtgtg | aacgagaacg | gcggctgtga | gcagtactgc | 420 |
| agtgaccaca | cgggcaccaa | gcgctcctgt | cggtgccacg | agggggtactc | tctgctggca | 480 |
| gacggggtgt | cctgcacacc | cacagttgaa | tatccatgtg | gaaaaatacc | tattctagaa | 540 |
| aaaagaaatg | ccagcaaacc | ccaaggccga | attgtggggg | gcaaggtgtg | ccccaaaggg | 600 |
| gagtgtccat | ggcaggtcct | gttgttggtg | aatggagctc | agttgtgtgg | ggggaccctg | 660 |
| atcaacacca | tctgggtggt | ctccgcggcc | cactgtttcg | acaaaatcaa | gaactggagg | 720 |
| aacctgatcg | cggtgctggg | cgagcacgac | ctcagcgagc | acgacgggga | tgagcagagc | 780 |

```
cggcgggtgg cgcaggtcat catccccagc acgtacgtcc cgggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctccccaaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag gtctcccag   1260 tacatcgagt ggctgcaaaa gctcatgcgc tcagagccac gccaggagt cctcctgcga   1320 gcccatttc ccgcgacgaa ggccgtgtgc attccgagga tcgacggccc agtgcagggc   1380
atcatcaatt tcgagcagaa ggaaagtaat ggaccagtga aggtgtgggg aagcattaaa   1440
ggactgactg aaggcctgca tggattccat gttcatgagt ttggagataa tacagcaggc   1500
tgtaccagtg caggtcctca ctttaatcct ctatccagaa acacggtgg gccaaaggat   1560 gaagagaggc atgttggaga cttgggcaat gtgactgctg acaaagatgg tgtggccgat   1620
gtgtctattg aagattctgt gatctcactc tcaggagacc attgcatcat tggccgcaca   1680
ctggtggtcc atgaaaaagc agatgacttg ggcaaggtg gaaatgaaga agtacaaag   1740 acaggaaacg ctggaagtcg tttggcttgt ggtgtaattg ggtga               1785

<210> SEQ ID NO 22
<211> LENGTH: 54
<212> TYPE: DNA
<213> ORGANISM: Artificial Sequence
<220> FEATURE:
<223> OTHER INFORMATION: Synthetic VIISOD1mutSS F

<400> SEQUENCE: 22
cccgcgacga aggccgtgtg cattccgagg atcgacggcc cagtgcaggg catc           54

<210> SEQ ID NO 23
<211> LENGTH: 54
<212> TYPE: DNA
<213> ORGANISM: Artificial Sequence
<220> FEATURE:
<223> OTHER INFORMATION: Synthetic FVIISOD1mutAS R

<400> SEQUENCE: 23
gatgccctgc actgggccgt cgatcctcgg aatgcacacg gccttcgtcg cggg           54

<210> SEQ ID NO 24
<211> LENGTH: 469
<212> TYPE: PRT
<213> ORGANISM: Artificial Sequence
<220> FEATURE:
<223> OTHER INFORMATION: Synthetic FactorVII-SOD1 1~25 IPRI

<400> SEQUENCE: 24

Met Val Ser Gln

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
            85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
            165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
            245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ala Thr Lys Ala
            435                 440                 445

Val Cys Ile Pro Arg Ile Asp Gly Pro Val Gln Gly Ile Ile Asn Phe
450                 455                 460

Glu Gln Lys Glu Ser
465

<210> SEQ ID NO 25
<211> LENGTH: 1410
<212> TYPE: DNA
<213> ORGANISM: Artificial Sequence
<220> FEATURE:
<223> OTHER INFORMATION: Synthetic FactorVII-SOD1 1~25 IPRI DNA

<400> SEQUENCE: 25

```
atggtctccc aggccctcag gctcctctgc cttctgcttg ggcttcaggg ctgcctggct      60
gcagtcttcg taacccagga ggaagcccac ggcgtcctgc accggcgccg gcgcgccaac     120
gcgttcctgg aggagctgcg gccgggctcc ctggagaggg agtgcaagga ggagcagtgc     180
tccttcgagg aggcccggga gatcttcaag gacgcggaga ggacgaagct gttctggatt     240
tcttacagtg atggggacca gtgtgcctca agtccatgcc agaatggggg ctcctgcaag     300
gaccagctcc agtcctatat ctgcttctgc ctccctgcct tcgagggccg gaactgtgag     360
acgcacaagg atgaccagct gatctgtgtg aacgagaacg gcggctgtga gcagtactgc     420
agtgaccaca cgggcaccaa cgctcctgt cggtgccacg aggggtactc tctgctggca     480
gacggggtgt cctgcacacc cacagttgaa tatccatgtg aaaaatacc tattctagaa     540
aaaagaaatg ccagcaaacc ccaaggccga attgtggggg gcaaggtgtg ccccaaaggg     600
gagtgtccat ggcaggtcct gttgttggtg aatggagctc agttgtgtgg ggggaccctg     660
atcaacacca tctgggtggt ctccgcggcc cactgtttcg acaaaatcaa gaactggagg     720
aacctgatcg cggtgctggg cgagcacgac ctcagcgagc acgacgggga tgagcagagc     780
cggcgggtgg cgcaggtcat catccccagc acgtacgtcc cgggcaccac caaccacgac     840
atcgcgctgc tccgcctgca ccagcccgtg gtcctcactg accatgtggt gcccctctgc     900
ctgcccgaac ggacgttctc tgagaggacg ctggccttcg tgcgcttctc attggtcagc     960
ggctggggcc agctgctgga ccgtggcgcc acggccctgg agctcatggt cctcaacgtg    1020
ccccggctga tgacccagga ctgcctgcag cagtcacgga aggtgggaga ctccccaaat    1080
atcacggagt acatgttctg tgccggctac tcggatggca gcaaggactc ctgcaagggg    1140
gacagtggag gccacatgc cacccactac cggggcacgt ggtacctgac gggcatcgtc    1200
agctggggcc agggctgcgc aaccgtgggc cactttgggg tgtacaccag ggtctcccag    1260
tacatcgagt ggctgcaaaa gctcatgcgc tcagagccac gcccaggagt cctcctgcga    1320
gccccatttc ccgcgacgaa ggccgtgtgc attccgagga tcgacggccc agtgcagggc    1380
atcatcaatt tcgagcagaa ggaaagttga                                    1410
```

<210> SEQ ID NO 26
<211> LENGTH: 34
<212> TYPE: DNA
<213> ORGANISM: Artificial Sequence
<220> FEATURE:
<223> OTHER INFORMATION: Synthetic SOD1-25XhoIAS R

<400> SEQUENCE: 26

```
ccgctcgagt caactttcct tctgctcgaa attg                                 34
```

<210> SEQ ID NO 27
<211> LENGTH: 534
<212> TYPE: PRT
<213> ORGANISM: Artificial Sequence
<220> FEATURE:
<223> OTHER INFORMATION: Synthetic FVII-SOD1 1-90 IPRI

<400> SEQUENCE: 27

-continued

```
Met Val Ser Gln Ala Leu Arg Leu Leu Cys Leu Leu Leu Gly Leu Gln
 1               5                  10                  15

Gly Cys Leu Ala Ala Val Phe Val Thr Gln Glu Glu Ala His Gly Val
             20                  25                  30

Leu His Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
 50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
             100                 105                 110

Ala Phe Glu Gly Arg Asn Cys Glu Thr His Lys Asp Asp Gln Leu Ile
         115                 120                 125

Cys Val Asn Glu Asn Gly Gly Cys Glu Gln Tyr Cys Ser Asp His Thr
     130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                 165                 170                 175

Pro Ile Leu Glu Lys Arg Asn Ala Ser Lys Pro Gln Gly Arg Ile Val
             180                 185                 190

Gly Gly Lys Val Cys Pro Lys Gly Glu Cys Pro Trp Gln Val Leu Leu
         195                 200                 205

Leu Val Asn Gly Ala Gln Leu Cys Gly Gly Thr Leu Ile Asn Thr Ile
     210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                 245                 250                 255

Asp Glu Gln Ser Arg Arg Val Ala Gln Val Ile Ile Pro Ser Thr Tyr
             260                 265                 270

Val Pro Gly Thr Thr Asn His Asp Ile Ala Leu Leu Arg Leu His Gln
         275                 280                 285

Pro Val Val Leu Thr Asp His Val Val Pro Leu Cys Leu Pro Glu Arg
     290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                 325                 330                 335

Val Leu Asn Val Pro Arg Leu Met Thr Gln Asp Cys Leu Gln Gln Ser
             340                 345                 350

Arg Lys Val Gly Asp Ser Pro Asn Ile Thr Glu Tyr Met Phe Cys Ala
         355                 360                 365

Gly Tyr Ser Asp Gly Ser Lys Asp Ser Cys Lys Gly Asp Ser Gly Gly
     370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                 405                 410                 415
```

```
Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ala Thr Lys Ala
        435                 440                 445

Val Cys Ile Pro Arg Ile Asp Gly Pro Val Gln Gly Ile Ile Asn Phe
    450                 455                 460

Glu Gln Lys Glu Ser Asn Gly Pro Val Lys Val Trp Gly Ser Ile Lys
465                 470                 475                 480

Gly Leu Thr Glu Gly Leu His Gly Phe His Val His Glu Phe Gly Asp
                485                 490                 495

Asn Thr Ala Gly Cys Thr Ser Ala Gly Pro His Phe Asn Pro Leu Ser
            500                 505                 510

Arg Lys His Gly Gly Pro Lys Asp Glu Glu Arg His Val Gly Asp Leu
        515                 520                 525

Gly Asn Val Thr Ala Asp
    530

<210> SEQ ID NO 28
<211> LENGTH: 1605
<212> TYPE: DNA
<213> ORGANISM: Artificial Sequence
<220> FEATURE:
<223> OTHER INFORMATION: Synthetic FVII-SOD1 1-90 IPRI DNA

<400> SEQUENCE: 28
atggtctccc aggccctcag gctcctctgc cttctgcttg gcttcagggg ctgcctggct      60
gcagtcttcg taacccagga ggaagcccac ggcgtcctgc accggcgccg cgcgccaac     120
gcgttcctgg aggagctgcg gccgggctcc ctggagaggg agtgcaagga ggagcagtgc    180
tccttcgagg aggcccggga gatcttcaag gacgcggaga ggacgaagct gttctggatt    240
tcttacagtg atgggaccca gtgtgcctca gtccatgcc agaatggggg ctcctgcaag    300
gaccagctcc agtcctatat ctgcttctgc ctccctgcct cgagggccg gaactgtgag    360
acgcacaagg atgaccagct gatctgtgtg aacgagaacg gcggctgtga gcagtactgc    420
agtgaccaca cgggcaccaa gcgctcctgt cggtgccacg aggggtactc tctgctggca    480
gacgggtgt cctgcacacc cacagttgaa tatccatgtg aaaaatacc tattctagaa      540
aaagaaatg ccagcaaacc caaggccga attgtggggg caaggtgtg ccccaaaggg       600
gagtgtccat ggcaggtcct gttgttggtg aatggagctc agttgtgtgg ggggaccctg    660
atcaacacca tctgggtggt ctccgcggcc cactgtttcg acaaaatcaa gaactggagg    720
aacctgatcg cggtgctggg cgagcacgac ctcagcgagc acgacgggga tgagcagagc    780
cggcgggtgg cgcaggtcat catccccagc acgtacgtcc gggcaccac caaccacgac    840
atcgcgctgc tccgcctgca ccagcccgtg gtcctcactg accatgtggt gcccctctgc    900
ctgcccgaac ggacgttctc tgagaggacg ctggccttcg tgcgcttctc attggtcagc    960
ggctggggcc agctgctgga ccgtggcgcc acggccctgg agctcatggt cctcaacgtg   1020
ccccggctga tgacccagga ctgcctgcag cagtcacgga aggtgggaga ctcccccaat   1080
atcacggagt acatgttctg tgccggctac tcggatggca gcaaggactc ctgcaagggg   1140
gacagtggag gcccacatgc cacccactac cggggcacgt ggtacctgac gggcatcgtc   1200
agctggggcc agggctgcgc aaccgtgggc cactttgggg tgtacaccag gtctcccag    1260
tacatcgagt ggctgcaaaa gctcatgcgc tcagagccac gccaggagt cctcctgcga   1320
gccccatttc ccgcgacgaa ggccgtgtgc gtgctgaagg cgacggccc agtgcaggc    1380
```

```
atcatcaatt tcgagcagaa ggaaagtaat ggaccagtga aggtgtgggg aagcattaaa    1440
ggactgactg aaggcctgca tggattccat gttcatgagt ttggagataa tacagcaggc    1500
tgtaccagtg caggtcctca ctttaatcct ctatccagaa aacacggtgg gccaaaggat    1560
gaagagaggc atgttggaga cttgggcaat gtgactgctg actga                    1605
```

<210> SEQ ID NO 29
<211> LENGTH: 34
<212> TYPE: DNA
<213> ORGANISM: Artificial Sequence
<220> FEATURE:
<223> OTHER INFORMATION: Synthetic SOD1-90XhoIAS R

<400> SEQUENCE: 29

```
ccgctcgagt cagtcagcag tcacattgcc caag                                 34
```

<210> SEQ ID NO 30
<211> LENGTH: 154
<212> TYPE: PRT
<213> ORGANISM: Homo sapiens
<220> FEATURE:
<223> OTHER INFORMATION: Human SOD1

<400> SEQUENCE: 30

```
Ala Thr Lys Ala Val Cys Val Leu Lys Gly Asp Gly Pro Val Gln Gly
  1               5                  10                  15

Ile Ile Asn Phe Glu Gln Lys Glu Ser Asn Gly Pro Val Lys Val Trp
                 20                  25                  30

Gly Ser Ile Lys Gly Leu Thr Glu Gly Leu His Gly Phe His Val His
             35                  40                  45

Glu Phe Gly Asp Asn Thr Ala Gly Cys Thr Ser Ala Gly Pro His Phe
         50                  55                  60

Asn Pro Leu Ser Arg Lys His Gly Gly Pro Lys Asp Glu Glu Arg His
     65                  70                  75                  80

Val Gly Asp Leu Gly Asn Val Thr Ala Asp Lys Asp Gly Val Ala Asp
                 85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln Leu
145                 150
```

<210> SEQ ID NO 31
<211> LENGTH: 149
<212> TYPE: PRT
<213> ORGANISM: Homo sapiens
<220> FEATURE:
<223> OTHER INFORMATION: Human SOD1 1-149

<400> SEQUENCE: 31

```
Ala Thr Lys Ala Val Cys Val Leu Lys Gly Asp Gly Pro Val Gln Gly
  1               5                  10                  15

Ile Ile Asn Phe Glu Gln Lys Glu Ser Asn Gly Pro Val Lys Val Trp
                 20                  25                  30

Gly Ser Ile Lys Gly Leu Thr Glu Gly Leu His Gly Phe His Val His
             35                  40                  45
```

```
Glu Phe Gly Asp Asn Thr Ala Gly Cys Thr Ser Ala Gly Pro His Phe
 50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp Lys Asp Gly Val Ala Asp
             85                  90                  95

Val Ser Ile Glu Asp Ser Val Ile Ser Leu Ser Gly Asp His Cys Ile
             100                 105                 110

Ile Gly Arg Thr Leu Val Val His Glu Lys Ala Asp Asp Leu Gly Lys
         115                 120                 125

Gly Gly Asn Glu Glu Ser Thr Lys Thr Gly Asn Ala Gly Ser Arg Leu
     130                 135                 140

Ala Cys Gly Val Ile
145

<210> SEQ ID NO 32
<211> LENGTH: 90
<212> TYPE: PRT
<213> ORGANISM: Homo sapiens
<220> FEATURE:
<223> OTHER INFORMATION: Human SOD1 1-90

<400> SEQUENCE: 32

Ala Thr Lys Ala Val Cys Val Leu Lys Gly Asp Gly Pro Val Gln Gly
 1               5                  10                  15

Ile Ile Asn Phe Glu Gln Lys Glu Ser Asn Gly Pro Val Lys Val Trp
             20                  25                  30

Gly Ser Ile Lys Gly Leu Thr Glu Gly Leu His Gly Phe His Val His
         35                  40                  45

Glu Phe Gly Asp Asn Thr Ala Gly Cys Thr Ser Ala Gly Pro His Phe
 50                  55                  60

Asn Pro Leu Ser Arg Lys His Gly Gly Pro Lys Asp Glu Glu Arg His
 65                  70                  75                  80

Val Gly Asp Leu Gly Asn Val Thr Ala Asp
             85                  90

<210> SEQ ID NO 33
<211> LENGTH: 25
<212> TYPE: PRT
<213> ORGANISM: Homo sapiens
<220> FEATURE:
<223> OTHER INFORMATION: Human SOD1 1-25

<400> SEQUENCE: 33

Ala Thr Lys Ala Val Cys Val Leu Lys Gly Asp Gly Pro Val Gln Gly
 1               5                  10                  15

Ile Ile Asn Phe Glu Gln Lys Glu Ser
             20                  25

<210> SEQ ID NO 34
<211> LENGTH: 534
<212> TYPE: PRT
<213> ORGANISM: Artificial Sequence
<220> FEATURE:
<223> OTHER INFORMATION: Synthetic FVII-SOD1 1-90

<400> SEQUENCE: 34

-continued

```
Gly Cys Leu Ala Ala Val Phe Val Thr Gln Glu Glu Ala His Gly Val
             20                  25                  30

Leu His Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
     50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ala Thr Lys Ala
```

```
                435                 440                 445
Val Cys Val Lys Gly Asp Gly Pro Val Gln Gly Ile Ile Asn Phe
450                 455                 460

Glu Gln Lys Glu Ser Asn Gly Pro Val Lys Val Trp Gly Ser Ile Lys
465                 470                 475                 480

Gly Leu Thr Glu Gly Leu His Gly Phe His Val His Glu Phe Gly Asp
                485                 490                 495

Asn Thr Ala Gly Cys Thr Ser Ala Gly Pro His Phe Asn Pro Leu Ser
                500                 505                 510

Arg Lys His Gly Gly Pro Lys Asp Glu Glu Arg His Val Gly Asp Leu
                515                 520                 525

Gly Asn Val Thr Ala Asp
                530

<210> SEQ ID NO 35
<211> LENGTH: 469
<212> TYPE: PRT
<213> ORGANISM: Artificial Sequence
<220> FEATURE:
<223> OTHER INFORMATION: Synthetic FVII-SOD1 1-25

<400> SEQUENCE: 35

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Ala Asn Ala Phe Leu Glu Glu Leu Arg Pro
            35                  40                  45

Gly Ser Leu Glu Arg Glu Cys Lys Glu Glu Gln Cys Ser Phe Glu Glu
        50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
```

```
                        260                 265                 270
Val Pro Gly Thr Thr Asn His Asp Ile Ala Leu Leu Arg Leu His Gln
                275                 280                 285
Pro Val Val Leu Thr Asp His Val Val Pro Leu Cys Leu Pro Glu Arg
                290                 295                 300
Thr Phe Ser Glu Arg Thr Leu Ala Phe Val Arg Phe Ser Leu Val Ser
305                 310                 315                 320
Gly Trp Gly Gln Leu Leu Asp Arg Gly Ala Thr Ala Leu Glu Leu Met
                325                 330                 335
Val Leu Asn Val Pro Arg Leu Met Thr Gln Asp Cys Leu Gln Gln Ser
                340                 345                 350
Arg Lys Val Gly Asp Ser Pro Asn Ile Thr Glu Tyr Met Phe Cys Ala
                355                 360                 365
Gly Tyr Ser Asp Gly Ser Lys Asp Ser Cys Lys Gly Asp Ser Gly Gly
                370                 375                 380
Pro His Ala Thr His Tyr Arg Gly Thr Trp Tyr Leu Thr Gly Ile Val
385                 390                 395                 400
Ser Trp Gly Gln Gly Cys Ala Thr Val Gly His Phe Gly Val Tyr Thr
                405                 410                 415
Arg Val Ser Gln Tyr Ile Glu Trp Leu Gln Lys Leu Met Arg Ser Glu
                420                 425                 430
Pro Arg Pro Gly Val Leu Leu Arg Ala Pro Phe Pro Ala Thr Lys Ala
                435                 440                 445
Val Cys Val Leu Lys Gly Asp Gly Pro Val Gln Gly Ile Ile Asn Phe
                450                 455                 460
Glu Gln Lys Glu Ser
465

<210> SEQ ID NO 36
<211> LENGTH: 4
<212> TYPE: PRT
<213> ORGANISM: Artificial Sequence
<220> FEATURE:
<223> OTHER INFORMATION: Partial sequence at positions 7 through 10 of
      human SOD1

<400> SEQUENCE: 36

Val Leu Lys Gly
  1

<210> SEQ ID NO 37
<211> LENGTH: 4
<212> TYPE: PRT
<213> ORGANISM: Artificial Sequence
<220> FEATURE:
<223> OTHER INFORMATION: Synthetic construct

<400> SEQUENCE: 37

Ile Pro Arg Ile
  1
```

BLOOD COAGULATION FACTOR VII AND VIIA DERIVATIVES, CONJUGATES AND COMPLEXES COMPRISING THE SAME, AND USE THEREOF

CROSS REFERENCE TO RELATED APPLICATIONS

This application is a National Stage of International Application No. PCT/KR2012/008102 filed Oct. 5, 2012, claiming priority based on Korean Patent Application No. 10-2011-0102099, filed Oct. 6, 2011, the contents of all of which are incorporated herein by reference in their entirety.

TECHNICAL FIELD

The present invention relates to a blood coagulation factor VII derivative, a blood coagulation factor VIIa derivative, FacVII and FacVIIa conjugates each prepared by linking a polymer capable of extending the blood half-life to the derivative, FacVII and VIIa complexes each prepared by linking a carrier to the conjugate, genes encoding the FacVII and FacVIIa derivatives, expression vectors comprising the genes, transformants introduced with the expression vectors, a method for preparing the FacVII and FacVIIa derivatives using the transformants, a method for preparing the FacVIIa conjugate and complex, a FacVIIa complex prepared by the method, a pharmaceutical composition for preventing or treating hemophilia comprising the derivative, conjugate, or complex as an active ingredient, and a pharmaceutical composition for promoting blood coagulation comprising the derivative, conjugate, or complex as an active ingredient. Further, the present invention relates to a method for preventing or treating hemophilia or for promoting blood coagulation, comprising administering to a subject a therapeutically effective amount of the composition.

BACKGROUND ART

At present, there are an estimated 140 thousand people with hemophilia worldwide, showing an annual increase of 20%. Genetically, hemophilia occurs in one out of every ten thousand, but diagnosis or treatment is made only for approximately 25% of all patients. Based on etiology, hemophilia is largely divided into two types: one is hemophilia A that is caused by a lack of blood coagulation factor VII (Factor VII, FacVII) and accounts for 80% of the total hemophilia patients, and the other is hemophilia B that is caused by a lack of blood coagulation factor XI (Factor XI) and accounts for 20% of the total hemophilia patients. For the treatment of hemophilia, external administration of blood coagulation factors is given, but this treatment method is problematic in that 10-15% of all hemophilia A patients develop antibodies against the blood coagulation factor, and 1-3% of all hemophilia B patients develop antibodies against the blood coagulation factor.

On the other hand, FacVII, which is a cause of hemophilia A accounting for more than a half of the hemophilia patients, is an enzyme that is mainly produced in the liver and composed of 406 amino acids, and includes gamma-carboxylation of glutamic acid at position 10, N-glycosylation of asparagines at positions 145 and 322, and O-glycosylation of serines at positions 52 and 60. Further, FacVII has two EGF-like domains and one serine protease domain, and single-chain FacVII is activated through cleavage between arginine at position 152 and isoleucine at position 153 to generate two-chain FacVIIa consisting of a light chain and a heavy chain. Since activated FacVIIa acts through auxiliary blood clotting mechanism, unlike other blood coagulation factors, antibodies are not produced even though injection of high-dose FacVIIa. Therefore, it can be used for the treatment of hemophilia A patients as well as patients having antibodies against FacVII due to the conventional therapies, and is known as a means of addressing the above described problems.

However, antibodies against FacVIIa are not produced, but there is another problem of requiring high-dose, frequent administration because of a short blood half-life. Because of the short half-life, FacVIIa should be administered 2-3 times a day for the treatment of hemophilia, and this frequent administration also becomes a serious obstacle to the prevention of hemophilia. In order to solve the problem of short blood half-life, studies have suggested the known microencapsulation, liposome encapsulation, and a variety of chemical modifications, but successful outcomes have not been reported yet. In particular, chemical modifications have been attempted such that the lysine residue or N-terminus on the surface of FacVIIa is chemically modified, or a carrier capable of extending blood half-life such as polyethylene glycol, albumin, transferrin, and immunoglobulin fragment is linked thereto, or a cysteine residue is inserted into a region not directly affecting the activity of FacVIIa to promote binding with other carrier. However, chemical modification of the lysine residue or N-terminus on the surface of FacVIIa reduces the ability of FacVIIa to bind with the membrane of platelet. When it is linked to other carrier, the carrier interferes with enzymatic activities. Insertion of cysteine residue induces formation of non-specific disulfide bond, consequently leading to a reduction in enzymatic activities. As such, many studies have been made to develop derivatives having an improved blood half-life without reducing the activity of FacVIIa, but no successful results have been reported yet.

rVIIa-FP (CSL Behring) prepared by fusion of albumin to the C-terminus of FacVIIa is in the pre-clinical phase, and its blood half-life in rats was increased to 6.7 times higher than that of the native FacVIIa. However, it still has a very short half-life of 4.38 hrs, and thus is not suitable for the treatment and prevention of hemophilia. PEGLip-FVIIa (Omri) prepared by using a pegylated liposome formulation is also in the pre-clinical phase, but its blood half-life was only 2 times higher than that of the native FacVIIa.

Two products, MAXY-VII (Bayer/Maxygen) prepared by Gla domain mutation and hyperglycosylation of FacVIIa to have a prolonged blood half-life and NN7128 (Novo/Neose) prepared by 40K PEG glycosylation to have a prolonged blood half-life are under clinical studies, but their blood half-life was only 5 times higher than that of the native FacVIIa. Thus, they are not suitable for the effective treatment and prevention of hemophilia.

DISCLOSURE

Technical Problem

Based on this background, the present inventors have made many efforts to develop derivatives having improved blood half-life while retaining the maximum activities of FacVII and FacVIIa. As a result, they found that a derivative prepared by fusion of a part of the SOD1 (Superoxide Dismutase 1) sequence to the C-terminus of FacVII is easily able to bind with a carrier capable of extending the blood half-life such as polyethylene glycol, albumin, transferrin, and immunoglobulin fragment without reducing the activity of FacVII or FacVIIa, and in particular, an immunoglobulin Fc region, a non-peptidyl polymer, and a FacVII or FacVIIa derivative are site-specifically linked via a covalent bond to minimize the activity reduction and to remarkably increase the blood half-life of the conjugate, thereby completing the present invention.

Technical Solution

An object of the present invention is to provide a derivative of FacVII or its active form FacVIIa which has an amino acid sequence of blood coagulation factor VII (Factor VII, FacVII) or its active form, blood coagulation factor VIIa (Factor VIIa, FacVIIa) and a peptide linker at the C-terminus.

Another object of the present invention is to provide a polynucleotide encoding the derivative of FacVII or its active form FacVIIa.

Still another object of the present invention is to provide an expression vector comprising the polynucleotide.

Still another object of the present invention is to provide a transformant introduced with the expression vector.

Still another object of the present invention is to provide a method for preparing the derivative of FacVII or its active form FacVIIa using the transformant.

Still another object of the present invention is to provide a conjugate of FacVII or its active form FacVIIa, which is prepared by linking a polymer capable of extending the blood half-life to the peptide linker of the derivative.

Still another object of the present invention is to provide a complex of FacVII or its active form FacVIIa, which is prepared by linking a carrier capable of extending the blood half-life to one end of the conjugate.

Still another object of the present invention is to provide a method for preparing the FacVIIa complex comprising the step of activating the FacVII complex.

Still another object of the present invention is to provide a FacVIIa complex prepared by the above method.

Still another object of the present invention is to provide a pharmaceutical composition for the prevention or treatment of hemophilia, comprising the derivative, conjugate or complex as an active ingredient.

Still another object of the present invention is to provide a pharmaceutical composition for blood coagulation, comprising the derivative, conjugate, or complex as an active ingredient.

Still another object of the present invention is to provide a method for preventing or treating hemophilia, comprising the step of administering to a subject a therapeutically effective amount of the pharmaceutical composition for the prevention or treatment of hemophilia.

Still another object of the present invention is to provide a method for promoting blood coagulation, comprising the step of administering to a subject a therapeutically effective amount of the pharmaceutical composition for blood coagulation.

Advantageous Effects

The FacVII or FacVIIa derivative of the present invention is able to bind with a carrier capable of improving the blood half-life while maintaining the activity of FacVII or FacVIIa, and they can be widely used in the development of effective prophylactic or therapeutic agent for hemophilia.

BEST MODE

Figure 1A:
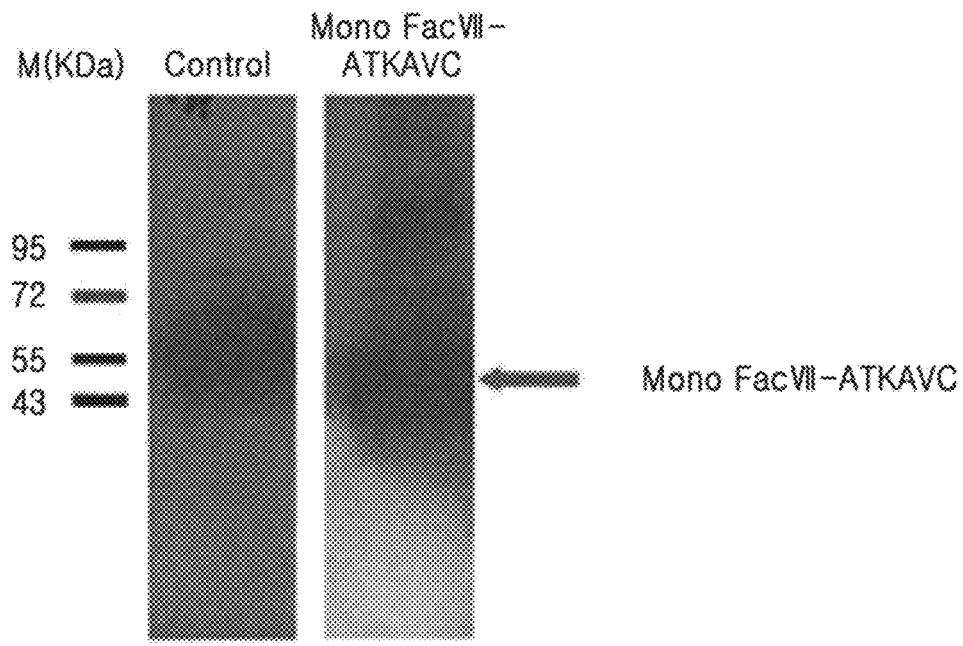
FIG. 1a is a photograph showing the result of Western blot analysis of FacVII-ATKAVC expressed in 293F cell line.
Figure 1B:
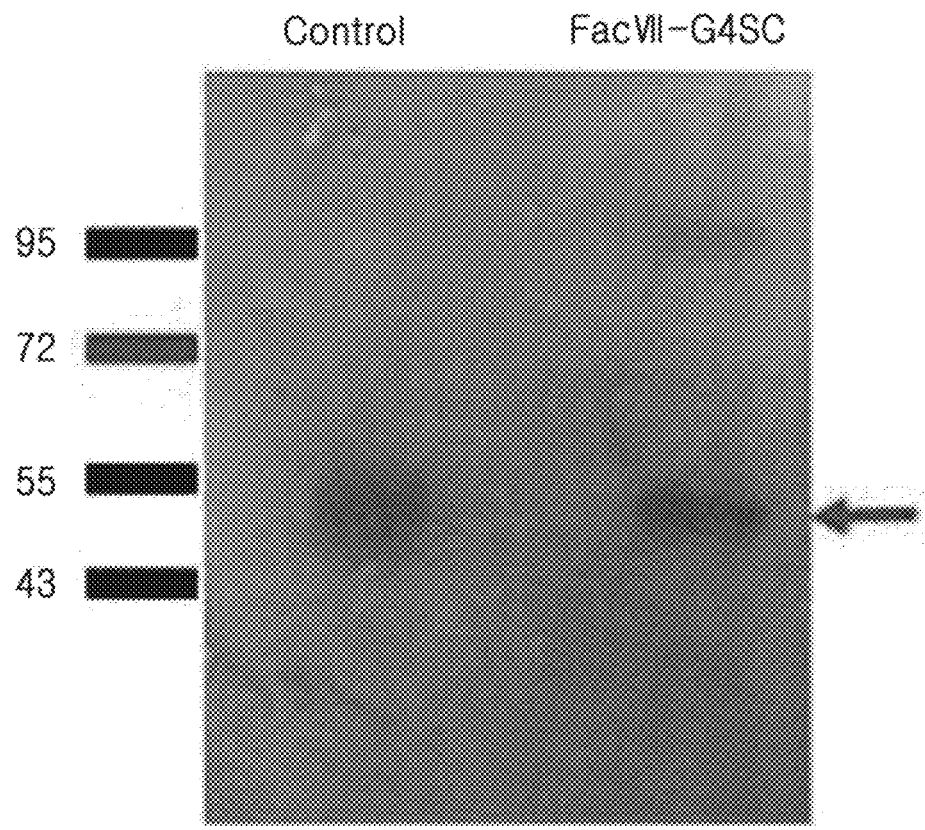
FIG. 1b is a photograph showing the result of Western blot analysis of a control group and FacVII-GGGGSC expressed in 293F cell line.
Figure 1C:
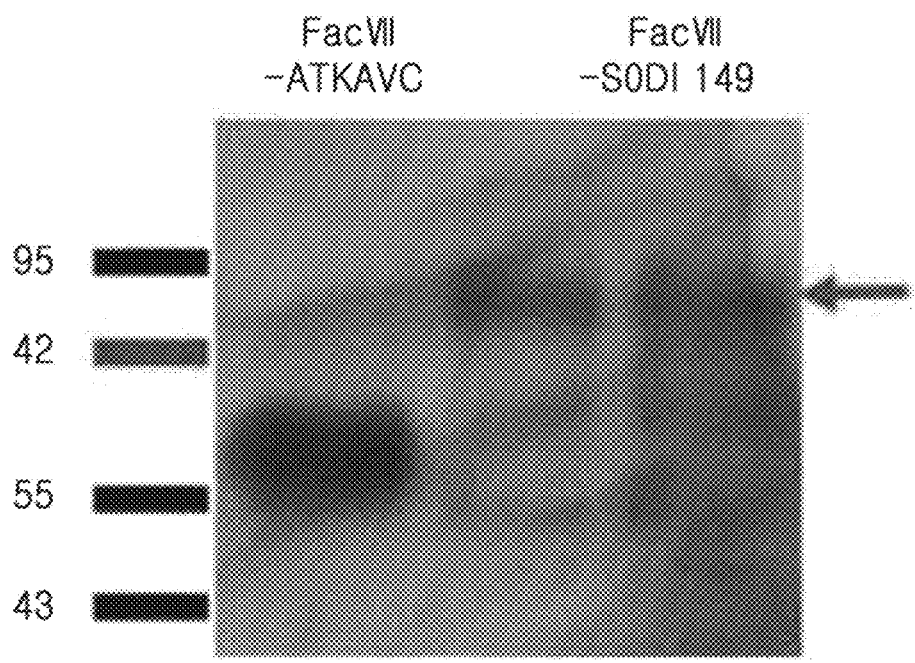
FIG. 1c is a photograph showing the result of Western blot analysis showing the molecular weight difference of FacVII-ATKAVC and FacVII-SOD1 1-149 expressed in 293F cell line.

In one aspect to achieve the above objects, the present invention provides a derivative of FacVII or its active form FacVIIa which has an amino acid sequence (SEQ ID NO. 4) of blood coagulation factor VII (Factor VII, FacVII) and a peptide linker at its C-terminus.

As used herein, the term "blood coagulation factor VII (Factor VII, FacVII)" is, also called proconvertin, one of the factors involved in blood coagulation, and has a size of 48 kDa, and it is encoded by a gene having a size of 12.8 kb, and mainly produced in the liver, and one of vitamin K-dependent plasma proteins. It has been known that FacVII binds to blood coagulation factor III on the surface of extravascular tissues such as serine protease precursor and smooth muscle cells, tumor tissues, or activated leukocytes, and thus activates blood coagulation factors IX and X, leading to initiation of the extrinsic blood coagulation. In the present invention, FacVII may include a native FacVII, chemically modified FacVII derivatives that retain the normal activity of the native FacVII, and variants that have at least 80% amino acid sequence homology, preferably 85%, 90%, or 95% amino acid sequence homology, and more preferably 98% or 99% amino acid sequence homology with the native FacVII while they retain the normal activity of the native FacVII. However, the sequence homology is not limited thereto, as long as they exhibit the activity of the native FacVII.

As used herein, the term "blood coagulation factor VIIa (Factor VIIa, FacVIIa)" means an active form of blood coagulation factor VII (Factor VII, FacVII), and single-chain FacVII is activated through cleavage between arginine at position 152 and isoleucine at position 153 to generate two-chain FacVIIa consisting of a light chain and a heavy chain. Since activated FacVIIa acts through auxiliary blood clotting mechanism, unlike other blood coagulation factors, antibodies are not produced even though injection of high-dose FacVIIa. In the present invention, FacVIIa may include a native FacVIIa, chemically modified FacVIIa derivatives that retain the normal activity of the native FacVIIa, and variants that have at least 80% amino acid sequence homology, preferably 85%, 90%, or 95% amino acid sequence homology, and more preferably 98% or 99% amino acid sequence homology with the native FacVII while they retain the normal activity of the native FacVIIa. However, the sequence homology is not limited thereto, as long as they exhibit the activity of the native FacVII.

As used herein, the term "linker" basically refers to a means capable of linking two different fusion partners (e.g., biological polymers) using a hydrogen bond, an electrostatic interaction, a van der Waals force, a disulfide bond, a salt bridge, a hydrophobic interaction, a covalent bond or the like. Preferably, it may have at least one cysteine involved in at least one disulfide bond under physiological conditions or other standard peptide conditions (e.g., peptide purification conditions, peptide storage conditions). It is possible to use the cysteine as a reactive group linking the fusion partner as well as the disulfide bond. In addition, the linker functions to provide a predetermined space between carriers or functions as a hinge providing the fusion protein with flexibility or rigidity as well as it simply functions to link each fusion partner. In the present invention, the linker is, but not particularly limited to, a peptide linker that links the C-terminus of FacVII or FacVIIa to link a carrier capable of extending the blood half-life, and preferably a C-terminal cysteine residue of peptide linker. It may be preferably a partial sequence (SEQ ID NO. 30) of SOD1 (Superoxide dismutase 1), more preferably, a partial sequence (SEQ ID NO. 31) selected from 1 to 149 of SOD1 sequence, much more preferably from 1 to 90 of SOD1 sequence (SEQ ID NO. 32), even much more preferably from 1 to 25 of SOD1 sequence (SEQ ID NO. 33), and most preferably from 1 to 6 of SOD1 sequence (SEQ ID NO. 5).

As used herein, the term "SOD1 (superoxide dismutase 1)" means an enzyme that catalyzes the disproportionation of the reactive oxygen, superoxide ion to oxygen and hydrogen peroxide, and is known to represent an important antioxidant defense in all cells exposed to oxygen. In the present invention, the SOD1 is used as a peptide linker capable of linking FacVII with the carrier capable of extending the blood half-life. SOD1 commonly found in the body is used as the linker, thereby reducing immunogenicity to the linker. VLKG (valine-leucine-lysine-glycine) (SEQ ID NO: 36) within the peptide linker SOD1 sequence may be replaced by a self-cleavage site sequence IPRI (isoleucine-proline-arginine-isoleucine)(SEQ ID NO: 37) that is recognized and cleaved by FacVIIa derivative. Owing to this replacement of the self-cleavage sequence, a linker region unnecessary for the activation can be removed by FacVIIa derivative upon activation.

In the present invention, the self-cleavage site is a site containing a particular sequence, in which a polypeptide possesses the corresponding particular sequence in its own sequence and recognizes and cleaves it.

As used herein, the term "FacVII derivative" means a modified FacVII that is composed of the amino acid sequence prepared by linking the peptide linker to the C-terminus of FacVII. The FacVII derivative of the present invention means the form prior to activation, and is changed to a FacVIIa derivative, when activated by a particular method. In the present invention, the FacVII derivative and FacVIIa derivative may have an equivalent meaning, except in a particular step, for example, a preparation process of a conjugate or the like. In the present invention, the FacVII derivative is, but not particularly limited to, a polypeptide (SEQ ID NO. 9) prepared by linking ATKAVC (SEQ ID NO. 5) from 1 to 6 of the SOD1 sequence to the C-terminus of FacVII derivative, a polypeptide (SEQ ID NO. 13) prepared by linking GGGGSC (SEQ ID NO. 10) to the C-terminus of FacVII derivative, a polypeptide (SEQ ID NO. 14) prepared by linking the amino acid sequence from 1 to 149 of the SOD1 sequence to the C-terminus of FacVII derivative, a polypeptide (SEQ ID NO. 34) prepared by linking the amino acid sequence from 1 to 90 of the SOD1 sequence to the C-terminus of FacVII derivative, a polypeptide (SEQ ID NO. 35) prepared by linking the amino acid sequence from 1 to 25 of the SOD1 sequence to the C-terminus of FacVII derivative, a polypeptide (SEQ ID NO. 20) prepared by linking the amino acid sequence from 1 to 149 of the mutated SOD1 sequence to the C-terminus of FacVII derivative, a polypeptide (SEQ ID NO. 27) prepared by linking the amino acid sequence from 1 to 90 of the mutated SOD1 sequence to the C-terminus of FacVII derivative, or a polypeptide (SEQ ID NO. 24) prepared by linking the amino acid sequence from 1 to 25 of the mutated SOD1 sequence to the C-terminus of FacVII derivative.

As used herein, the term "FacVIIa derivative" means an active form of the FacVII derivative, which has an amino acid sequence identical to that of the FacVII derivative, but is activated by cleavage between the amino acids at positions 152 and 153. In the present invention, the FacVIIa derivative is, but not particularly limited to, a polypeptide (SEQ ID NO. 9) prepared by linking ATKAVC (SEQ ID NO. 5) from 1 to 6 of the SOD1 sequence to the C-terminus of FacVIIa derivative, a polypeptide (SEQ ID NO. 13) prepared by linking GGGGSC (SEQ ID NO. 10) to the C-terminus of FacVIIa derivative, a polypeptide (SEQ ID NO. 14) prepared by linking the amino acid sequence from 1 to 149 of the SOD1 sequence to the C-terminus of FacVIIa derivative, a polypeptide (SEQ ID NO. 34) prepared by linking the amino acid sequence from 1 to 90 of the SOD1 sequence to the C-terminus of FacVII derivative, a polypeptide (SEQ ID NO. 35) prepared by linking the amino acid sequence from 1 to 25 of the SOD1 sequence to the C-terminus of FacVII derivative, a polypeptide (SEQ ID NO. 20) prepared by linking the amino acid sequence from 1 to 149 of the mutated SOD1 sequence to the C-terminus of FacVIIa derivative, a polypeptide (SEQ ID NO. 27) prepared by linking the amino acid sequence from 1 to 90 of the mutated SOD1 sequence to the C-terminus of FacVII derivative, or a polypeptide (SEQ ID NO. 24) prepared by linking the amino acid sequence from 1 to 25 of the mutated SOD1 sequence to the C-terminus of FacVIIa derivative.

The present inventors investigated the characteristics for the activated FacVII, and they intended to develop a derivative having the improved blood half-life without reducing the activity of FacVIIa. Non-activated FacVII is a single-chain FacVII by connecting light and heavy chains, and exposes only the N-terminus of light chain. However, when it becomes FacVIIa, the active site of heavy chain is exposed by cleavage between arginine at position 152 and isoleucine at position 153, and the exposed isoleucine at position 153 becomes the N-terminus of heavy chain. The N-terminus of heavy and light chains plays an important role in FacVIIa activation, and thus conjugation at the N-terminus may reduce the activity of FacVII, compared to the native FacVII.

For this reason, the present inventors provide a FacVII derivative prepared by using a fragment of the SOD1 peptide sequence as a linker, the peptide fragment containing cysteine that is not exposed structurally to the outside and thus is not involved in the disulfide bond. In addition, a self-cleavage site sequence that can be recognized and cleaved by FacVIIa derivative is inserted in the peptide fragment linked as a linker, and thus a linker unnecessary for the activation can be removed. The present invention provides a FacVII derivative that has a fragment containing free cysteine of the SOD1 peptide at the C-terminus. It was found that a dimeric form of the FacVII derivative is produced at the lowest level during incubation, and the FacVII derivative is able to easily form a conjugate with a carrier capable of extending the blood half-life, thereby making up for the disadvantages of the native FacVII and the derivatives prepared by simple insertion of cysteine into FacVIIa.

Therefore, a conjugate is prepared by linking to the C-terminus of the FacVII or FacVIIa derivative of the present invention a substance capable of remarkably improving the blood half-life, maintaining the blood coagulation function and remarkably increasing drug compliance, thereby preparing a product having more excellent effects of improving blood coagulation and preventing or treating hemophilia than the known products.

In another aspect, the present invent ion provides a polynucleotide encoding the FacVII derivative, an expression vector comprising the polynucleotide, a transformant that is introduced with the expression vector to express the FacVII derivative, and a method for preparing the FacVII derivative using the transformant.

The polynucleotide encoding the FacVII derivative provided in the present invention is, but not particularly limited to, a polynucleotide that is prepared by linking the FacVII-encoding region to the peptide linker-encoding region, and preferably a polynucleotide (SEQ ID NO. 8) encoding a polypeptide (SEQ ID NO. 9) that is prepared by linking ATKAVC (SEQ ID NO. 5) from 1 to 6 of the SOD1 sequence to the C-terminus of FacVII derivative, a polynucleotide (SEQ ID NO. 12) encoding a polypeptide (SEQ ID NO. 13) that is prepared by linking GGGGSC (SEQ ID NO. 10) to the C-terminus of FacVII derivative, a polynucleotide (SEQ ID NO. 15) encoding a polypeptide (SEQ ID NO. 14) that is prepared by linking 1 to 149 amino acids of the SOD1 sequence to the C-terminus of FacVII derivative, a polynucleotide (SEQ ID NO. 21) encoding a polypeptide (SEQ ID NO. 20) that is prepared by linking 1 to 149 amino acids of the mutated SOD1 sequence to the C-terminus of FacVII derivative, a polynucleotide (SEQ ID NO. 28) encoding a polypeptide (SEQ ID NO. 27) that is prepared by linking 1 to 90 amino acids of the mutated SOD1 sequence to the C-terminus of FacVII derivative, or a polynucleotide (SEQ ID NO. 25) encoding a polypeptide (SEQ ID NO. 24) that is prepared by linking 1 to 25 amino acids of the mutated SOD1 sequence to the C-terminus of FacVII derivative.

The expression vector comprising the polynucleotide encoding the FacVII derivative provided in the present invention is, but not particularly limited to, a vector capable of replicating and/or expressing the polynucleotide in eukaryotic or prokaryotic cells, including mammalian cells (e.g., human, monkey, rabbit, rat, hamster, mouse cells, etc.), plant cells, yeast cells, insect cells or bacterial cells (e.g., E. coli, etc.), and preferably a vector that is operably linked to a proper promoter to express the polynucleotide in a host cell and contains at least one selection marker. More preferably, it may be an expression vector prepared by introduction of the polynucleotide into a phage, a plasmid, a cosmid, a mini-chromosome, a viral vector, or a retroviral vector. Most preferably, it may be an expression vector pXOGC-FVII-ATKAVC including the FacVII derivative-encoding polynucleotide that is prepared by linking the polynucleotide encoding ATKAVC (SEQ ID NO. 5) from 1 to 6 of the SOD1 sequence to the 3'-terminus of FacVII gene, an expression vector pXOGC-FVII-GGGGSC including the FacVII derivative-encoding polynucleotide that is prepared by linking the polynucleotide encoding GGGGSC (SEQ ID NO. 10) to the 3'-terminus of FacVII gene, an expression vector pXOGC-FVII-SOD1 1-149 including the FacVII derivative-encoding polynucleotide that is prepared by linking the polynucleotide encoding the amino acid sequence (SEQ ID NO. 14) from 1 to 149 of the SOD1 sequence to the 3'-terminus of FacVII gene, an expression vector pXOGC-FVII-SOD1 IPRI including the FacVII derivative-encoding polynucleotide (SEQ ID NO. 21) that is prepared by linking the polynucleotide encoding 1 to 149 amino acids of the mutated SOD1 sequence to the 3'-terminus of FacVII gene, an expression vector pXOGC-FVII-SOD1 1-90 IPRI including the FacVII derivative-encoding polynucleotide (SEQ ID NO. 28) that is prepared by linking the polynucleotide encoding 1 to 90 amino acids of the mutated SOD1 sequence to the 3'-terminus of FacVII gene, or an expression vector pXOGC-FVII-SOD1 1-25 IPRI including the FacVII derivative-encoding polynucleotide (SEQ ID NO. 25) that is prepared by linking the polynucleotide encoding 1 to 25 amino acids of the mutated SOD1 sequence to the 3'-terminus of FacVII gene.

The transformant introduced with the expression vector provided in the present invention is, but not particularly limited to, bacterial cells such as E. coli, Streptomyces, and Salmonella typhimurium; yeast cells such as Pichia pastoris; insect cells such as Drosophila and Spodoptera Sf9 cells; animal cells such as CHO, COS, NSO 293, and Bowes melanoma cells; or plant cells, which are transformed by introduction of the expression vector. It may be preferably a transformant prepared by introduction of the expression vector into 293F or CHO cell line, and most preferably HMF709 prepared by introduction of the expression vector pXOGC-FVII-ATKAVC into CHO cell line.

The method for preparing the FacVII derivative provided in the present invention comprises the steps of (i) culturing the transformant so as to obtain a culture solution; and (ii) recovering the FacVII derivative from the culture solution.

The method further comprises the step of activating the recovered FacVII derivative, thereby preparing the FacVIIa derivative from the prepared FacVII derivative. The activation method is the same as described above.

The present inventors prepared an expression vector pXOGC-FVII-ATKAVC including the FacVII derivative-encoding polynucleotide that is prepared by linking the polynucleotide encoding ATKAVC (SEQ ID NO. 5) from 1 to 6 of the SOD1 sequence to the 3'-terminus of FacVII gene (Example 2-1), and the expression vector was introduced into 293F cell line (Example 3-1) or CHO cell line (Example 3-2) so as to obtain a transformant. Subsequently, the FacVII derivative was expressed from the transformant, and the expressed FacVII derivative was purified (Example 4, FIG. 2). The expressed FacVII derivative was activated to prepare the FacVIIa derivative, followed by comparison of its activity with that of native FacVIIa (Example 6 and FIG. 4). As a result, the FacVIIa derivative prepared from the FacVII derivative of the present invention was found to show the activity equivalent to that of native FacVIIa. Thus, a clone showing the highest expression level of FacVII derivative was selected from the transformants prepared by introduction of the expression vector pXOGC-FVII-ATKAVC into CHO cells, and was designated as "HMF709", and deposited at the Korean Collection for Type Culture, Korea Research Institute of Bioscience and Biotechnology (111 Gwahangno, Yuseong-gu, Daejeon, Korea) under accession number "KCTC12022BP".

Instill another aspect, the present invent ion provides a conjugate of FacVII or its active form FacVIIa which is prepared by linking a polymer capable of extending the blood half-life to the peptide linker of the FacVII derivative.

The polymer of the present invention may be a polymer such as polyethylene glycol capable of extending the blood half-life, and selected from protein carriers such as immunoglobulin fragment, transferrin, antibody, and albumin.

The present invention provides a conjugate that is prepared by linking the FacVII derivative with the protein carrier using a non-peptidyl polymer as a linker in vitro without using a genetic recombination method.

The non-peptidyl polymer of the present invention refers to a non-peptidyl polymer designed to resist to the degradation by various enzymes or immune molecules in the blood or serum. The non-peptidyl polymer which is not limited by the followed, may be selected from the group consisting of polyethylene glycol, polypropylene glycol, ethylene glycol-propylene glycol copolymers, polyoxyethylated polyols, polyvinyl alcohols, polysaccharides, dextrans, polyvinyl ethyl ethers, biodegradable polymers, lipid polymers, chitins, hyaluronic acids, and a combination thereof. And the non-peptidyl polymer can be linked to each other via any kind of covalent bond except peptide bond. Further, the derivatives thereof known in the art and derivatives easily prepared by any known technique in the art are also within the scope of the present invention. In the present invention, the non-peptidyl polymer may be linked to the peptide linker of the FacVII derivative or the FacVIIa derivative. The non-peptidyl polymer may be linked to the various binding sites of the peptide linker. Preferably, the non-peptidyl polymer may be linked to the C-terminus of peptide linker present at the FacVII derivative or the FacVIIa derivative.

The non-peptidyl polymer can comprise reactive group which may include, but is not limited to, a aldehyde, a propionaldehyde, a butyraldehyde, a maleimide or a succinimide (succinimidyl propionate, succinimidyl carboxymethyl, hydroxy succinimidyl, or succinimidyl carbonate). In addition, the non-peptidyl polymer may have a single reactive group or double reactive groups. If the non-peptidyl polymer comprises two or more reactive groups, it can be linked to the linker of FacVII derivative at one reactive group, and also linked to another carrier such as the antibodies, the immunoglobulin fragments, albumin, or transferrin at other reactive group. For example, when the non-peptidyl polymer has a reactive aldehyde group at one end and a maleimide, ortho pyridyl disulfide or thiol reactive group at the other end, non-specific reaction can be minimized, and it is effective in the selective binding of the FacVII derivative or the FacVIIa derivative and carrier at both ends of the non-peptidyl polymer. A final product produced by reductive alkylation due to the aldehyde bond may be more stable than an amide bond. In addition, the aldehyde reactive group selectively reacts with the amino terminus of the carrier at a low pH, and may form a covalent bond with a lysine residue at a high pH, for example, pH 9.0.

In still another aspect, the present invention provides a complex of FacVII or its active form FacVIIa which is prepared by linking the derivative of FacVII or its active form FacVIIa with an immunoglobulin Fc region via the non-peptidyl polymer.

The FacVII complex that is linked to a carrier such as antibody, immunoglobulin fragment, albumin, and transferrin, in particular, the immunoglobulin Fc via the non-peptidyl polymer may be prepared by the steps of (1) covalently linking a non-peptidyl polymer having an aldehyde or succinimide derivative reactive group at its one end to the amine group of immunoglobulin Fc; (2) recovering a conjugate that comprises the immunoglobulin Fc region covalently linked with the non-peptidyl polymer at the amine group, from the reaction mixture of step (1); (3) covalently linking the FacVII derivative to the other end of the non-peptidyl polymer having a maleimide, ortho pyridyl disulfide, or thiol reactive group in the recovered conjugate so as to produce a FacVII complex having the immunoglobulin Fc region and the FacVII derivative at each end of the non-peptidyl polymer; and (4) activating the FacVII conjugate produced in step (3) so as to produce a FacVIIa complex having FacVIIa and the immunoglobulin Fc region linked via the non-peptidyl polymer.

Further, the FacVII complex may be prepared by the steps of (1) covalently linking a non-peptidyl polymer having a maleimide, ortho pyridyl disulfide, or thiol reactive group at its one end to the C-terminal thiol group of FacVII derivative; (2) recovering a conjugate that includes the FacVII derivative covalently linked with the non-peptidyl polymer, from the reaction mixture of step (1); (3) covalently linking the immunoglobulin Fc region to the other end of the non-peptidyl polymer having an aldehyde or succinimide derivative reactive group in the recovered conjugate so as to produce a FacVII complex having the immunoglobulin Fc region and the FacVII derivative at each end of the non-peptidyl polymer; and (4) activating the FacVII conjugate produced in step (3) so as to produce a FacVIIa complex having FacVIIa and the immunoglobulin Fc region linked via the non-peptidyl polymer.

Further, the FacVIIa complex may be prepared by the steps of (1) covalently linking a non-peptidyl polymer having a maleimide, ortho pyridyl disulfide, or thiol reactive group at its one end to the C-terminal thiol group of FacVIIa derivative; (2) recovering a conjugate that includes the FacVII derivative covalently linked with the non-peptidyl polymer, from the reaction mixture of step (1); and (3) covalently linking the immunoglobulin Fc region to the other end of the non-peptidyl polymer having an aldehyde or succinimide derivative reactive group in the recovered conjugate so as to produce a FacVIIa complex having the immunoglobulin Fc region and the FacVIIa derivative at each end of the non-peptidyl polymer.

On the other hand, the non-peptidyl polymer may include two or three reactive ends, and the two or three reactive ends may be the same as or different from each other. For example, it may have a maleimide group at one end and an aldehyde group, a propionaldehyde group, or a butyraldehyde group at the other end. When poly(ethylene glycol) having hydroxy reactive groups at both ends thereof is used as the non-peptidyl polymer, the hydroxy group may be activated to various reactive groups by known chemical reactions, or a poly(ethylene glycol) having a commercially available modified reactive group may be used so as to prepare the FacVII conjugate and complex of the present invention.

Therefore, the non-peptidyl polymer included in the FacVII conjugate and complex of the present invention may be preferably a non-peptidyl polymer having a methyl group at one end and a maleimide, ortho pyridyl disulfide or thiol reactive group at the other end, and more preferably a non-peptidyl polymer having a maleimide, ortho pyridyl disulfide or thiol reactive group at one end and an aldehyde or succinimide derivative reactive group at the other end, and most preferably a non-peptidyl polymer having a maleimide reactive group and an aldehyde reactive group at both ends, respectively.

The FacVII derivative that is used in the preparation of the conjugate or complex using the FacVII derivative of the present invent ion may be an inactive form or an activated FacVIIa derivative. However, the use of FacVII is preferred in order to prevent degradation due to the activated FacVIIa during the conjugate preparation using the FacVIIa derivative.

As the carrier, the Fc regions may be obtained from native forms isolated from humans and other animals including cows, goats, pigs, mice, rabbits, hamsters, rats and guinea pigs. In addition, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins. Immunoglobulin Fc may be obtained from a native immunoglobulin by isolating whole immunoglobulins from human or animal organisms and treating them with a specific proteolytic enzyme, and also may be obtained from transformed cells by recombination technique. Preferably, it is a recombinant human immunoglobulin Fc region from *E. coli*. On the other hand, IgG is divided into IgG1, IgG2, IgG3 and IgG4 subclasses, and the present invention includes combinations and hybrids thereof. Preferred are the IgG2 and IgG4 subclasses, and most preferred is the Fc region of IgG4 rarely having effector functions such as CDC (complement dependent cytotoxicity).

That is, as the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The peptide linker which is used in the fusion protein obtained by a conventional inframe fusion method has drawbacks in that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without limitation, as long as it is a polymer having the aforementioned function, that is, a polymer having resistance to the in-vivo proteolytic enzyme. The non-peptidyl polymer has a molecular weight in the range of 1 to 100 kDa, and preferably of 1 to 40 kDa. The non-peptidyl polymer of the present invention, linked to the immunoglobulin Fc region, may be one polymer or a combination of different types of polymers.

In one embodiment of the present invention, in vitro activity of the FacVII conjugate was determined. The present invention is intended to minimize a reduction in the activity by site-specific conjugation of FacVII and the non-peptidyl polymer. Thus, the activities of FacVII-ATKAVC and FacVII-ATKAVC-40 kDa PEG were determined using the native FacVII and FacVII-40 kDa PEG as a control group (Example 7). As a result, it was found that in vitro activity of the N-terminal PEGylated FacVII-40 kDa PEG was approximately 11%, compared to that of FacVII, and in vitro activity of the C-terminal PEGylated FacVII-ATKAVC-40 kDa PEG was approximately 29%, compared to that of FacVII-ATKAVC. That is, the C-terminal PEGylated FacVII-ATKAVC-40 kDa PEG maintains an activity approximately 2.5 times higher than $EC_{50}$ of the N-terminal PEGylated FacVII-40 kDa PEG, indicating that the FacVII activity can be maintained at a higher level by site-specific conjugation using ATKAVC (Table 2).

In another embodiment, in vitro activity of the complex prepared by linking the non-peptidyl polymer and the immunoglobulin Fc region to the FacVII conjugate was determined (Example 8). As a result, it was found that in vitro activity of FacVIIa-ATKAVC-PEG-Fc was approximately 45%, compared to that of FacVIIa-ATKAVC (Table 3), indicating that the complex linked with the non-peptidyl polymer and the immunoglobulin Fc region has the carrier capable of improving the blood half-life while maintaining the FacVII activity, thereby being widely used in the development of more effective prophylactic or therapeutic agent for hemophilia.

In still another aspect, the present invention provides a method for preparing a FacVIIa conjugate comprising the step of activating the FacVII conjugate, and a FacVIIa conjugate prepared by the method. In detail, the method for preparing the FacVIIa conjugate may comprise the steps of (i) covalently linking a non-peptidyl polymer capable of extending the blood half-life to the C-terminal thiol group of the FacVII derivative; (ii) recovering the FacVII conjugate that is composed of the non-peptidyl polymer linked to the FacVII derivative; and (iii) activating the recovered FacVII conjugate so as to produce a FacVIIa conjugate having the non-peptidyl polymer linked to the FacVIIa region.

In addition, the method comprises the steps of (i) covalently linking the non-peptidyl polymer capable of extending the blood half-life to the C-terminal thiol group of the FacVIIa derivative; and (ii) recovering the FacVIIa conjugate that is composed of the non-peptidyl polymer linked to the FacVIIa derivative so as to produce a FacVIIa conjugate having the non-peptidyl polymer linked to the FacVIIa region.

The non-peptidyl polymer capable of extending the blood half-life used in the method is the same as described above, and the method for activating FacVII or FacVII conjugate is, but not particularly limited to, an on-column activation (auto-activation) of activating the FacVII or FacVII conjugate by attaching it to an anion exchange column or an in-solution activation of activating the FacVII or FacVII conjugate by reacting it in a solution phase. In particular, the on-column activation is also called solid-phase activation, and is performed by "auto-activation" after attachment of the FacVII or FacVII conjugate to the anion exchange column without additional components. In contrast, the in-solution activation is a method of inducing FacVII activation, considering various factors needed in FacVII activation, for example, calcium ion concentration, pH, temperature, and FacVII concentration.

The present inventors demonstrated that the blood half-life of the conjugate prepared by linking the immunoglobulin fragment to the native FacVII via the non-peptidyl linker was increased to approximately 200 times, compared to the native FacVII having no immunoglobulin fragment (Korean Patent Application No. 2010-0062860). It is well known that the increased half-life is not attributed to FacVII, but attributed to the non-peptidyl linker and the immunoglobulin fragment. Therefore, the conjugate prepared by using the prepared FacVII derivative is also expected to have the increased half-life.

In still another aspect, the present invention provides a pharmaceutical composition for the prevention or treatment of hemophilia or a pharmaceutical composition for blood coagulation, comprising the derivative of FacVII or its active form FacVIIa, the conjugate of FacVII or its active form FacVIIa, the complex of FacVII or its active form FacVIIa, as an active ingredient.

In addition, the present invention provides a method for preventing or treating hemophilia or for promoting blood coagulation, comprising administering to a subject a therapeutically effective amount of the pharmaceutical composition.

As used herein, the term "prevention" means all of the actions by which the occurrence of hemophilia is restrained or retarded by concurrent administration of the composition of the present invention, and the term "treatment" means all of the actions by which the symptoms of diabetes have taken a turn for the better or been modified favorably by concurrent administration of the composition of the present invention.

In the present invention, the method for promoting blood coagulation is to promote the action of blood coagulation factor by preparation of derivatives, conjugates, or complexes having remarkably increased blood half-life from blood coagulation factor FacVIIa or its active form FacVIIa having a short half-life.

Further, the pharmaceutical composition of the present invention may include a pharmaceutically acceptable carrier. As used herein, the term "pharmaceutically acceptable carrier" refers to a carrier or diluent that does not cause significant irritation to an organism and does not abrogate the biological activity and properties of the administered compound. For oral administration, the pharmaceutically acceptable carrier may include a binder, a lubricant, a disintegrant, an excipient, a solubilizer, a dispersing agent, a stabilizer, a suspending agent, a coloring agent, and a flavor. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multi-dose container or an ampule as a single-dose dosage form. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavors, and antiseptics.

In still another aspect, the present invention provides a method for treating hemophilia, comprising administering to a subject having hemophilia a therapeutically effective amount of the pharmaceutical composition for the prevention or treatment of hemophilia including the derivative, conjugate, or complex as an active ingredient. In this regard, the pharmaceutical composition may be administered alone or in combinations with other therapeutic agents simultaneously or sequentially.

As used herein, the term "administration" means introduction of a predetermined amount of a substance into a patient by a certain suitable method. The composition may be administered via any of the common routes, as long as it is able to reach a desired tissue. A variety of modes of administration are contemplated, including intraperitoneal, intravenous, intramuscular, subcutaneous, intradermal, oral, topical, intranasal, intrapulmonary and intrarectal, but the present invention is not limited to these exemplified modes of administration. However, since peptides are digested upon oral administration, active ingredients of a composition for oral administration should be coated or formulated for protection against degradation in the stomach. Preferably, the multimer may be administered in an injectable form. In addition, the pharmaceutical composition may be administered using a certain apparatus capable of transporting the active ingredients into a target cell.

Further, the pharmaceutical composition of the present invention can be determined by several related factors including the types of diseases to be treated, administration routes, the patient's age, gender, weight and severity of the illness, as well as by the types of the drug used as an active component.

The pharmaceutical composition of the present invention shows excellent in-vivo duration of efficacy and titer, thereby remarkably reducing the number and frequency of administration thereof for preventing or treating hemophilia or for promoting blood coagulation.

MODE FOR INVENTION

Hereinafter, the present invention will be described in more detail with reference to Examples. However, these Examples are for illustrative purposes only, and the invention is not intended to be limited by these Examples.

Example 1

Preparation of FacVII Gene-Containing Expression Vector

First, human Factor VII gene containing a signal sequence was obtained using a Polymerase Chain Reaction (PCR) technique. For amplification of Factor VII (FacVII) gene, a human fetal liver cDNA library (TAKARA BIO USA) was used as a template, and forward and reverse primers of the following SEQ ID NOs. 1 and 2 were used to perform PCR (95° C. 1 minute denaturation; 30 cycles (95° C. 30 seconds, 60° C. 30 seconds and 68° C. 90 seconds); 68° C. 5 minutes). At this time, for easy cloning, the recognition site for the restriction enzyme BamHI was inserted into the primer of SEQ ID NO. 1 and the recognition site for the restriction enzyme XhoI was inserted into the primer of SEQ ID NO. 2. Subsequently, a nucleotide sequence (SEQ ID NOs. 3 and 4) of the PCR product of approximately 1.3 kb obtained by PCR was examined.

```
VIIBHISS F:
                                          (SEQ ID NO. 1)
5'-cccggatccatggtctcccaggccctcaggctcc-3'

VIIXhoIAS R:
                                          (SEQ ID NO. 2)
5'-gggctcgagctagggaaatggggctcgcagg-3'
```

In order to express the obtained PCR product under the control of CMV promoter, it was cloned into an animal cell expression vector pXOGC. The pXOGC vector is an expression vector including one or more CCGCCC repeat sequence-removed DHFR promoter and a DHFR-encoding nucleotide sequence operably linked thereto (Korean Patent No. 880509). Specifically, the PCR product was digested with the restriction enzymes, BamHI and XhoI at 37° C. for 2 hours, and applied to a PCR purification kit (Qiagen, USA) so as to obtain the cleaved DNA fragment. The DNA fragment was mixed with the pXOGC vector treated with the restriction enzymes BamHI and XhoI, and cloned using T4 DNA ligase, thereby preparing an expression vector including FacVII gene.

Example 2

Preparation of Expression Vector for Expression of Various Recombinant FacVII Derivatives The FacVII gene-containing expression vector (pXOGC-FVII) prepared in Example 1 was used to obtain a polynucleotide encoding a FacVII derivative which has a partial sequence of SOD1 (Superoxide Dismutase 1, SEQ ID NO. 30) at the C-terminus of FacVII, and an expression vector capable of expressing the derivative was prepared.

Example 2-1

Preparation of Recombinant FacVII Derivative-Expressing Vector, pXOGC-FVII-ATKAVC A recombinant FacVII derivative-expressing vector pXOGC-FVII-ATKAVC, which contains a polynucleotide further having a polynucleotide encoding the sequence from 1 to 6 of the SOD1 sequence at the 3-terminus of FacVII gene included in the expression vector pXOGC-FVII prepared in Example 1, was prepared. In detail, the expression vector pXOGC-FVII was used as a template, and forward and reverse primers of the following SEQ ID NOs. 6 and 7 were used to perform PCR (95° C. 1 minute denaturation; 30 cycles (95° C. 60 seconds, 60° C. 60 seconds and 68° C. 90 seconds); 68° C. 5 minutes). At this time, for easy cloning, the recognition site for the restriction enzyme EcoRI was inserted into the primer of SEQ ID NO. 6 and the recognition site for the restriction enzyme XhoI was inserted into the primer of SEQ ID NO. 7. Subsequently, a nucleotide sequence (SEQ ID NO. 8) of the PCR product of approximately 1.4 kb obtained by PCR was examined.

```
FVIIEcoRISS F (SEQ ID NO. 6):
5'-ccggaattcatggccaacgcgttcctggaggagctgcggccgggc-3'

FVII#1XhoIAS R (SEQ ID NO. 7):
5'-ccgctcgagtcagcacacggccttcgtcgcgggaaatggggctcgc aggaggactcctgggc-3'
```

In order to express the obtained PCR product under the control of CMV promoter, it was cloned into an animal cell expression vector pXOGC. Specifically, the PCR product was digested with the restriction enzymes, EcoRI and XhoI at 37° C. for 2 hours, and applied to a PCR purification kit so as to obtain the cleaved DNA fragment. The DNA fragment was mixed with the pXOGC vector treated with the restriction enzymes EcoRI and XhoI, and cloned using T4 DNA ligase, thereby preparing an expression vector (pXOGC-FVII-ATKAVC) having a FacVII derivative-encoding polynucleotide, which contains a polynucleotide encoding the sequence ATKAVC (SEQ ID NO. 5) from 1 to 6 of the SOD1 sequence linked at the 3'-terminus of FacVII gene.

Example 2-2

Preparation of Recombinant FacVII Derivative-Expressing Vector, pXOGC-FVII-GGGGSC A recombinant FacVII derivative-expressing vector pXOGC-FVII-GGGGSC, which contains a polynucleotide further having a polynucleotide encoding 6 amino acids (GGGGSC, SEQ ID NO. 10) at the 3'-terminus of FacVII gene included in the expression vector pXOGC-FVII prepared in Example 1, was prepared. To achieve this, PCR was performed in the same manner as in Example 2-1, except using forward and reverse primers of SEQ ID NOs. 6 and 11 and a nucleotide sequence (SEQ ID NO. 12) of the PCR product of approximately 1.4 kb was examined. Subsequently, an expression vector (pXOGC-FVII-GGGGSC), which contains the FacVII derivative-encoding polynucleotide having a polynucleotide encoding GGGGSC (SEQ ID NO. 10) at the 3'-terminus of FacVII gene, was prepared in the same manner as in Example 2-1, except using the PCR product.

```
FVII#2XhoIAS R (SEQ ID NO. 11):
5'-ccgctcgagtcagcaggagccgccgccgccgggaaatggggctcgc aggaggactcctgggc-3'
```

Example 2-3

Preparation of Recombinant FacVII Derivative-Expressing Vector, pXOGC-FVII-SOD1 1-149

A recombinant FacVII derivative-expressing vector pXOGC-FVII-SOD1 1-149, which contains a polynucleotide (SEQ ID NO. 15) further having a polynucleotide encoding 1 to 149 amino acids of the SOD1 (Superoxide dismutase 1) sequence at the 3'-terminus of FacVII gene included in the expression vector pXOGC-FVII prepared in Example 1, was prepared.

In detail, the FacVII DNA sequence (SEQ ID NO. 3) was used as a template, and a FacVII forward primer (SEQ ID NO. 16) and a FacVII reverse primer (SEQ ID NO. 17) were used to perform PCR (95° C. 1 minute denaturation; 30 cycles (95° C. 60 seconds, 60° C. 60 seconds and 68° C. 90 seconds); 68° C. 5 minutes). At this time, for easy cloning, the recognition site for the restriction enzyme EcoRI was inserted into the primer of SEQ ID NO. 16 and a partial sequence of 5'-terminus of SOD1 was contained in the primer of SEQ ID NO. 17. As a result, a first PCR fragment was obtained.

```
FVIIEcoRISS F:
                                    (SEQ ID NO. 16)
5'-ccggaattcatggtctcccaggccctcaggctcc-3'

FVIISODInfAS R:
                                    (SEQ ID NO. 17)
5'-cggccttcgtcgcgggaaatggggctcgcaggag-3'
```

Next, SOD1 cDNA (RC200725, OriGene, USA) was used as a template, and an SOD1 forward primer (SEQ ID NO. 18) and an SOD1 reverse primer (SEQ ID NO. 19) were used to perform PCR (95° C. 1 minute denaturation; 30 cycles (95° C. 60 seconds, 60° C. 60 seconds and 68° C. 40 seconds); 68° C. 5 minutes). At this time, for easy cloning, a partial sequence of 3'-terminus of FacVII was contained in the primer of SEQ ID NO. 18 and the recognition site for the restriction enzyme XhoI was inserted into the primer of SEQ ID NO. 19. As a result, a second PCR fragment was obtained.

FVIISODInfSS F:
(SEQ ID NO. 18)
5'-gagccccatttcccgcgacgaaggccgtgtgcgt-3'

SODXhoIAS R:
(SEQ ID NO. 19)
5'-ccgctcgagtcaaattacaccacaagccaaacga-3'

The first and second PCR fragments thus obtained were used as a template and a FacVII forward primer (SEQ ID NO. 16) and a SOD1 reverse primer (SEQ ID NO. 19) were used to perform second PCR. Finally, a third PCR fragment was obtained (95° C. 1 minute denaturation; 30 cycles (95° C. 60 seconds, 60° C. 60 seconds and 68° C. 120 seconds); 68° C. 5 minutes).

In order to express the obtained third PCR product under the control of CMV promoter, it was cloned into an animal cell expression vector pXOGC. Specifically, the third PCR product was digested with the restriction enzymes, EcoRI and XhoI at 37° C. for 2 hours, and applied to a PCR purification kit so as to obtain the cleaved DNA fragment. The DNA fragment was mixed with the pXOGC vector treated with the restriction enzymes EcoRI and XhoI, and cloned using T4 DNA ligase, thereby preparing an expression vector (pXOGC-FVII-SOD1 1-149) having a FacVII derivative-encoding polynucleotide, which contains a polynucleotide encoding the amino acids from 1 to 149 of the SOD1 sequence linked at the 3'-terminus of FacVII gene.

Example 2-4

Preparation of Recombinant FacVII Derivative-Expressing Vector, pXOGC-FVII-SOD1 IPRI It was intended to insert a self-cleavage site of FacVII into the SOD1 gene included in the expression vector pXOGC-FVII-SOD1 1-149 prepared in Example 2-3. To achieve this, prepared was a recombinant FacVII derivative-expressing vector pXOGC-FVII-SOD1 IPRI which contains a polynucleotide (SEQ ID NO. 21) encoding an amino acid sequence (SEQ ID NO. 20) prepared by linking 1-149 amino acids of SOD1 mutated by replacement of 7 to 10 amino acids (VLKG) (SEQ ID NO: 36) of SOD1 in 451-454 amino acids of FacVII-SOD1 1-149 (SEQ ID NO. 14) with IPRI (SEQ ID NO: 37), to the C-terminus of FacVII.

In detail, the third PCR fragment obtained in Example 2-3 was used as a template and forward and reverse primers (SEQ ID NOs. 22 and 23) were used to perform PCR. Finally, a fourth PCR fragment was obtained (95° C. 30 seconds denaturation; 18 cycles (95° C. 30 seconds, 55° C. 60 seconds and 68° C. 9 minutes); 68° C. 9 minutes).

A nucleotide sequence (SEQ ID NO. 21) of the fourth PCR product of approximately 9 kb was examined.

VIISOD1mutSS F:
(SEQ ID NO. 22)
5'-cccgcgacgaaggccgtgtgcattccgaggatcgacggcccagtgc
agggcatc-3'

FVIISOD1mutAS R:
(SEQ ID NO. 23)
5'-gatgccctgcactgggccgtcgatcctcggaatgcacacggccttc
gtcgcggg-3'

Subsequently, the fourth PCR product was digested with the restriction enzyme DpnI at 37° C. for 1 hour to cleave a non-mutated sequence, and cloned by transformation into *E. coli* so as to prepare an expression vector (pXOGC-FVII-SOD1 IPRI) which contains a polynucleotide encoding a FacVII derivative having 1-149 amino acids of the mutated SOD1 at the C-terminus of FacVII.

Example 2-5

Preparation of Recombinant FacVII Derivative-Expressing Vector pXOGC-FVII-SOD1 1-25 IPRI Prepared was a recombinant FacVII derivative-expressing vector pXOGC-FVII-SOD1 1-25 IPRI which contains a polynucleotide (SEQ ID NO. 25) encoding an amino acid sequence (SEQ ID NO. 24) prepared by linking 1-25 amino acids of SOD1 mutated by replacement of 7 to 10 amino acids (VLKG) (SEQ ID NO: 36) of SOD1 with IPRI (SEQ ID NO: 37) to the C-terminus of FacVII.

In detail, the expression vector pXOGC-FVII-SOD1 IPRI prepared in Example 2-4 was used as a template, and forward and reverse primers (SEQ ID NOs. 16 and 26) were used to perform PCR (95° C. 1 minute denaturation; 30 cycles (95° C. 60 seconds, 60° C. 60 seconds and 68° C. 90 seconds); 68° C. 5 minutes). Finally, a fifth PCR fragment was obtained.

SOD1-25XhoIAS R:
(SEQ ID NO. 26)
5'-ccgctcgagtcaactttccttctgctcgaaattg-3'

Subsequently, the fifth PCR product was digested with the restriction enzymes EcoRI and XhoI at 37° C. for 2 hour, and applied to a PCR purification kit so as to obtain the cleaved DNA fragment. The DNA fragment was mixed with the pXOGC vector treated with the restriction enzymes EcoRI and XhoI, and cloned using T4 DNA ligase, thereby preparing an expression vector (pXOGC-FVII-SOD1 1-25 IPRI) containing a polynucleotide encoding a FacVII derivative having 1 to 25 amino acids of the mutated SOD1 sequence linked at the C-terminus of FacVII gene.

Example 2-6

Preparation of Recombinant FacVII Derivative-Expressing Vector, pXOGC-FVII-SOD1 1-90 IPRI Prepared was a recombinant FacVII derivative expression vector pXOGC-FVII-SOD1 1-90 IPRI which contains a polynucleotide (SEQ ID NO. 28) encoding an amino acid sequence (SEQ ID NO. 27) prepared by linking 1-90 amino acids of SOD1 mutated by replacement of 7 to 10 amino acids (VLKG) (SEQ ID NO: 36) of SOD1 with IPRI (SEQ ID NO: 37) to the C-terminus of FacVII.

In detail, the expression vector pXOGC-FVII-SOD1 IPRI prepared in Example 2-4 was used as a template, and forward and reverse primers (SEQ ID NOs. 16 and 29) were used to perform PCR (95° C. 1 minute denaturation; 30 cycles (95° C. 60 seconds, 60° C. 60 seconds and 68° C. 100 seconds); 68° C. 5 minutes). Finally, a fifth PCR fragment was obtained.

```
SOD1-90XhoIAS R:
                                      (SEQ ID NO. 29)
5'-ccgctcgagtcagtcagcagtcacattgcccaag-3'
```

Subsequently, the fifth PCR product was digested with the restriction enzymes EcoRI and XhoI at 37° C. for 2 hour, and applied to a PCR purification kit so as to obtain the cleaved DNA fragment. The DNA fragment was mixed with the pXOGC vector treated with the restriction enzymes EcoRI and XhoI, and cloned using T4 DNA ligase, thereby preparing an expression vector (pXOGC-FVII-SOD1 1-90 IPRI) containing a polynucleotide encoding a FacVII derivative having 1 to 90 amino acids of the mutated SOD1 sequence linked at the C-terminus of FacVII gene.

Example 3

Expression of FacVII Derivatives

A variety of FacVII derivatives were expressed using each expression vector prepared in Example 2.

Example 3-1

Expression of FacVII Derivatives in 293F Cell Line

An expression vector having nothing at the C-terminus of FacVII (control), and expression vectors (pXOGC-FVII-SOD1 1-149, pXOGC-FVII-SOD1 1-25 IPRI, pXOGC-FVII-SOD1 1-90 IPRI, pXOGC-FVII-ATKAVC or pXOGC-FVII-GGGGSC), each expression vector having a polynucleotide prepared by fusion of SOD1 1-149 sequence, mutated SOD1 1-25 sequence, mutated SOD1 1-90 sequence, SOD1 1-6 sequence, or GGGGSC sequence at the C-terminus of FacVII, were introduced into Freestyle™ 293 F cell line (Invitrogen, cat. no. R79007) to prepare each transformant. Different FacVII derivatives were expressed from each transformant.

To achieve this, the 293F cell line was sub-cultured every other day while it cultured at 37° C. and 8% $CO_2$ with shaking at a speed of 120 rpm or higher. When the number of cultured cells reached $10\times10^5$ cells/ml and the viability was 85% or more, each expression vector prepared in Example 2 was introduced thereto so as to obtain transformants. In detail, 500 μl of Freestyle™ max reagent, 500 μg of each expression vector, and 10 ml of Optipro™ SFM (Invitrogen, cat. no. 12309-050) were added to 500 ml of Freestyle™ 293 expression medium (Invitrogen, cat. no. 12338-018) having $10\times10^5$ cells/ml of cells, and mixed and left at room temperature for 10 minutes for introduction of each expression vector into 293F cell line. Thereafter, 50 μg of vitamin K essential for FacVII activation was added thereto, and cultured at 37° C. and 8% $CO_2$ with shaking at a speed of 120 rpm or higher for 3 days. After completion of the culture, the cells were centrifuged at 3000 rpm for 5 minutes to obtain the supernatants. Each FacVII derivative included in the supernatant was collected and purified. Subsequently, Western blotting was performed using anti-FacVII antibody to detect each expressed FacVII derivative (FIGS. 1*a* to 1*c*).

FIG. 1*a* is a photograph showing the result of Western blot analysis of FacVII-ATKAVC expressed in 293F cell line, in which M is a size marker (Prestained protein ladder, fermentas), Lane 1 is the result of Western blot analysis of FacVII-ATKAVC under reducing conditions, and Lane 2 is the result of Western blot analysis of FacVII-ATKAVC under non-reducing conditions. As shown in FIG. 1*a*, approximately 20 to 30% of a dimeric form was detected under non-reducing conditions, and no dimeric form was detected under reducing conditions.

Further, FIG. 1*b* is a photograph showing the result of Western blot analysis of a control group and FacVII-GGGGSC expressed in 293F cell line, and FIG. 1*c* is a photograph showing the result of Western blot analysis showing the molecular weight difference of FacVII-ATKAVC and FacVII-SOD1 1-149 expressed in 293F cell line.

As shown in FIGS. 1*b* and 1*c*, it was found that a variety of FacVII derivatives can be normally produced in 293F cell line.

Example 3-2

Expression of FacVII Derivative (pXOGC-FVII-ATKAVC) in CHO Cell Line

The expression vector pXOGC-FVII-ATKAVC prepared in Example 2-1 was introduced into DG44/CHO cell line (CHO/dhfr−) that is deficient in DHFR to show incomplete DNA synthesis (Urlaub et al., Somat. Cell. Mol. Genet., 12, 555-566, 1986) to obtain a transformant, and FacVII-ATKAVC derivative was expressed from the transformant.

In detail, the DG44/CHO cell line was cultured to reach 80 to 90% confluence, and the cells were washed with Opti-MEM (Gibco, cat. No. 51985034) three times.

On the other hand, a mixture of 3 ml of Opti-MEM and 5 μg of expression vector pXOGC-FVII-ATKAVC, and a mixture of 3 ml of Opti-MEM and 20 μl of lipofectamine (Gibco, cat. no. 18324-012) were left at room temperature for 30 minutes, respectively. Subsequently, the mixtures were mixed, and added to the cultured DG44/CHO cell line. Then, the cells were cultured at 37° C. and 5% $CO_2$ for approximately 18 hours, resulting in introduction of the expression vector pXOGC-FVII-ATKAVC into DG44/CHO cell line. Subsequently, the cultured cells were washed with 10% FBS-supplemented DMEM-F12 (Gibco, cat. no. 11330) three times, and then the medium was added thereto, followed by cultivation for 48 hours. The cultured cells were detached by trypsin treatment, and they were inoculated into MEM-α medium (WELGENE, cat. no. LM008-02)) containing 10% FBS and 1 mg/ml of G418 (Cellgro, cat. no. 61-234-RG) without selection medium (HT supplement (Hypoxanthine-Thymidine)). Until the transformed cells survived to form colonies, the medium was replaced with the selection medium every 2 or 3 days. Thus, the transformed cells were selected from the separated cells. At this time, in order to increase the expression level of FacVII-ATKAVC derivative in the selected transformed cells, 10 nM MTX (Sigma, cat. no. M8407) was added to the selection medium to gradually increase the concentration, and 2 to 3 weeks later, the content of MTX was increased up to 30 nM.

Furthermore, in order to reduce heterogeneity of the transformed cells, a limiting dilution method was performed to obtain single clones. In detail, the transformed cells were diluted to a ratio of 0.7 cell in each well of a 96-well plate, and cultured for 2 to 3 weeks to examine whether single clones were observed. When cluster formation of single clones were observed in wells, the single clones were transferred to a 24-well plate, and cell growth rate of each clone and expression level of FacVII derivative were analyzed by ELISA so as to select a clone showing the highest expression level of FacVII derivative. It was designated as "HMF709", and deposited at the Korean Collection for Type Culture, Korea Research Institute of Bioscience and Biotechnology (111 Gwahangno, Yuseong-gu, Daejeon, Korea) on Sep. 23, 2011 under accession number "KCTC12022BP".

Example 4

Purification of FacVII-ATKAVC

The transformant prepared in Example 3-2 was cultured to express FacVII-ATKAVC, and the culture solution was centrifuged at 3000 rpm for 5 minutes to obtain a supernatant.

The supernatant was filtered using a 0.2 µm microfiltration membrane, and 0.6 M ammonium sulfate was added thereto, and the mixture was applied to a butyl HP column. Elution was performed using a concentration gradient buffer solution (20 mM Tris-HCl pH 7.5) containing 0.6-0 M ammonium sulfate to obtain an active fraction containing FacVII-ATKAVC.

The buffer solution of the obtained active fraction was replaced with a 10 mM sodium phosphate buffer solution (pH 7.0), which was applied to a Heparin HP column and eluted using a 0-1.0 M NaCl concentration gradient buffer solution (10 mM sodium phosphate, pH 7.0) so as to obtain an active fraction containing FacVII-ATKAVC.

The active fraction was concentrated, and applied to a Superdex75 column, and then eluted using 150 mM NaCl 20 mM Tris-HCl (pH 7.5) buffer solution so as to obtain an active fraction containing FacVII-ATKAVC. The buffer solution of the obtained active fraction was replaced with a 2 mM benzamidine 20 mM Tris-HCl (pH 7.5) buffer solution, which was applied to a Q FF column. Then, washing (2 mM benzamidine 0.2 M NaCl 20 mM Tris-HCl (pH 8.0) buffer), re-equilibration (2 mM benzamidine 0.1 M NaCl 20 mM Tris-HCl (pH 8.0) buffer), and concentration-gradient elution (2 mM benzamidine 25 mM NaCl 35 mM $CaCl_2$, 20 mM Tris-HCl (pH 8.0) buffer) were performed to purify FacVII-ATKAVC.

Figure 2:
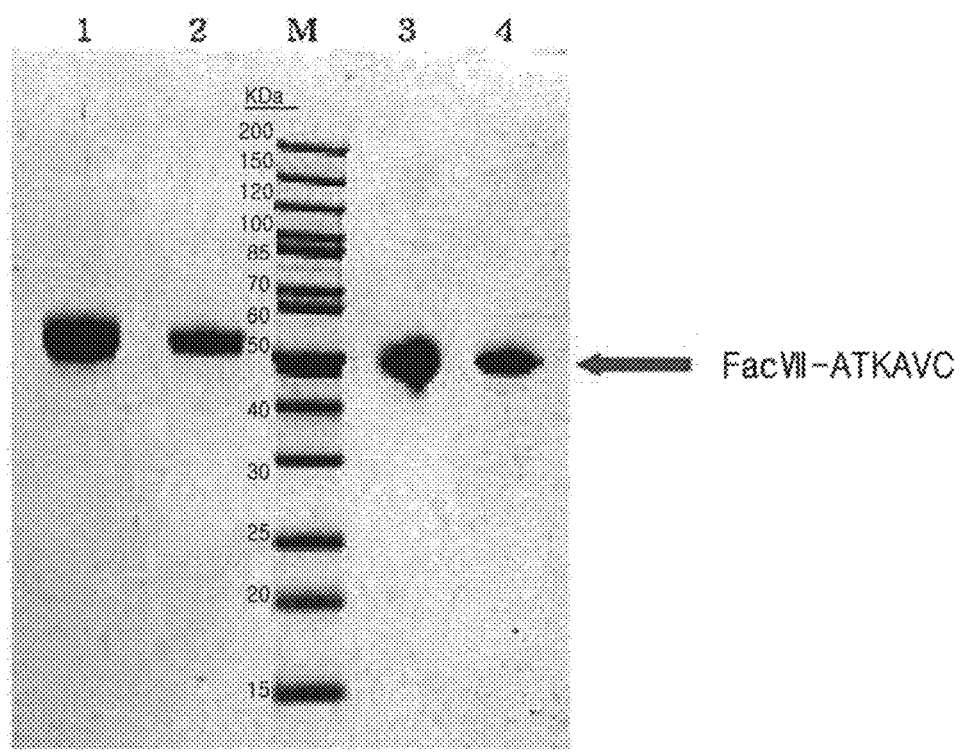
FIG. 2 is a photograph showing the result of electrophoresis of the purified FacVII-ATKAVC.

The purity of the purified FacVII-ATKAVC was examined by SDS PAGE (FIG. 2). FIG. 2 is a photograph showing the result of electrophoresis of the purified FacVII-ATKAVC, in which M is a size marker, Lane 1 is FacVIII under reducing conditions, Lane 2 is of FacVII-ATKAVC under reducing conditions, Lane 3 is FacVII under non-reducing conditions, and Lane 4 is FacVII-ATKAVC under non-reducing conditions.

Example 5

Preparation of Conjugates of FacVII-ATKAVC and PEG

FacVII-ATKAVC purified in Example 4 was conjugated with PEG having different molecular weights to prepare conjugates.

Example 5-1

Preparation of FacVII-ATKAVC-40 kDa PEG Conjugate

Figure 3:
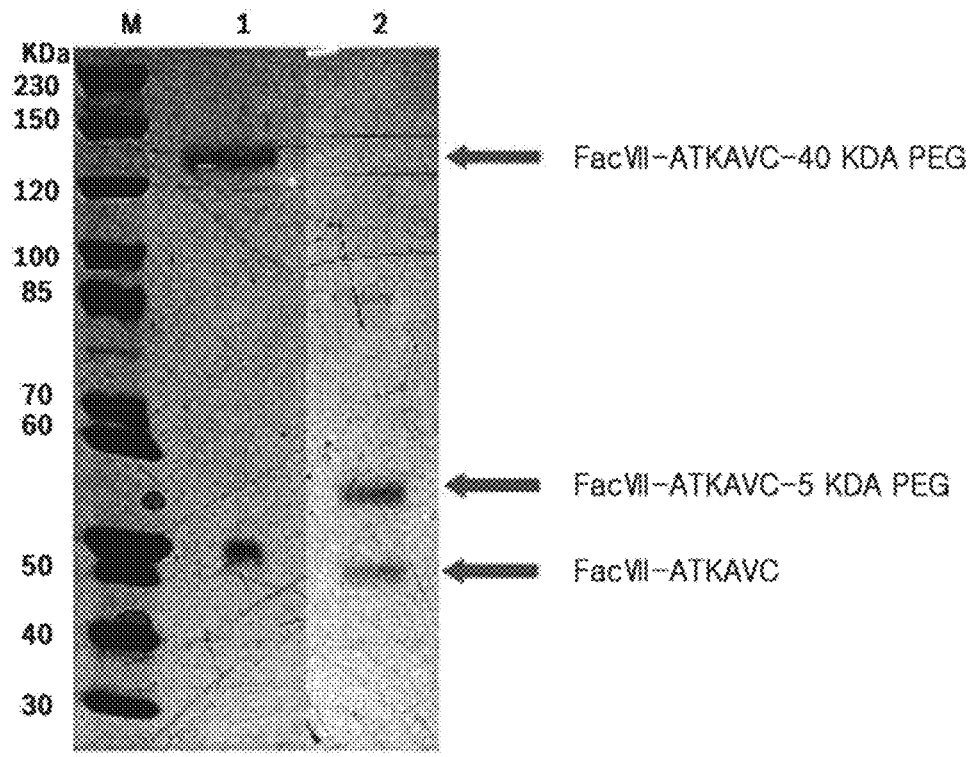
FIG. 3 is a photograph showing the result of electrophoresis of a FacVII-ATKAVC-PEG conjugate.

For PEGylation of the C-terminus of FacVII-ATKAVC with 40 kDa mPEG-maleimide (NOF, Japan), FacVII-ATKAVC (1 mg/ml) and 40 kDa mPEG-maleimide were mixed at a molar ratio of 1:20 in the presence of a 100 mM phosphate buffer solution (pH 5.5), and a reducing agent, 2 mM triarylphosphine was added thereto, and reacted at 25° C. for 2 hours. As a result, mono-PEGylated FacVII-ATKAVC (FacVII-ATKAVC-40k PEG conjugate) was prepared (FIG. 3). FIG. 3 is a photograph showing the result of electrophoresis of a conjugate of FacVII-ATKAVC and PEG, in which M is a size marker, Lane 1 is FacVII-ATKAVC-40 kDa PEG conjugate under non-reducing conditions, and Lane 2 is FacVII-ATKAVC-5 kDa PEG conjugate under non-reducing conditions.

Example 5-2

Preparation of FacVII-ATKAVC-5 kDa PEG Conjugate

PEGylation of the C-terminus of FacVII-ATKAVC with aldehyde-5 kDa PEG-maleimide (NOF, Japan) was performed in the same manner as in Example 5-1, except using aldehyde-5 kDa PEG-maleimide instead of 40 kDa mPEG-maleimide so as to prepare PEGylated FacVII-ATKAVC (FacVII-ATKAVC-5 kDa PEG conjugate) (FIG. 3).

Example 5-3

Preparation of FacVIIa-ATKAVC-PEG-Fc Complex

To link the aldehyde reactive group of maleimide-10 kDa PEG-aldehyde (NOF, Japan) to the N-terminus of immunoglobulin Fc region, the immunoglobulin Fc region and maleimide-10 kDa PEG-aldehyde were mixed at a molar ratio of 1:1 in the presence of 100 mM phosphate buffer solution (pH 6.0), and a reducing agent, 20 mM Na—$CNBH_3$ was added under the condition of a protein concentration of 10 mg/ml. The mixture was reacted at low temperature (4~8° C.) for 2 hours. In order to obtain a mono-PEGylated immunoglobulin Fc region (maleimide-10 kDa PEG-Fc), cation exchange chromatography was performed using Source 15Q, and elution was performed in a 20 mM Tris buffer solution (pH 7.5) using a sodium chloride concentration gradient.

On the other hand, the C-terminus of FacVII-ATKAVC was reduced in a 10 mM Glycil-Glycine buffer solution (pH 5.5) using a reducing agent, 0.5~2 mM triphenylphosphine-3,3',3"-trisulfonic trisodium salt hydrate at room temperature for 2 hours.

The C-terminus-reduced FacVII-ATKAVC and the mono-PEGylated immunoglobulin Fc region (maleimide-10 kDa PEG-Fc) were mixed at a molar ratio of 1:4~1:20, and reacted at room temperature for 2 hours in the presence of 50 mM Tris buffer solution (pH 7.5) at a total protein concentration of 1~2 mg/ml. First, cation exchange chromatography was performed using Source 15Q, and a FacVII-ATKAVC-10k PEG-Fc complex was eluted in a 20 mM Tris buffer solution (pH 7.5) using a sodium chloride concentration gradient.

For activation of FacVII in the FacVII-ATKAVC-PEG-Fc complex, solution reaction was performed in a 0.1 M Tris-HCl buffer solution (pH 8.0) at approximately 4 mg/ml based on FacVII at low temperature (4~8° C.) for 18 hours.

Size exclusion chromatography was performed using Superdex200 and a 10 mM Glycil-Glycine buffer solution (pH 5.5) so as to purify final FacVIIa-ATKAVC-PEG-Fc.

Figure 4A:
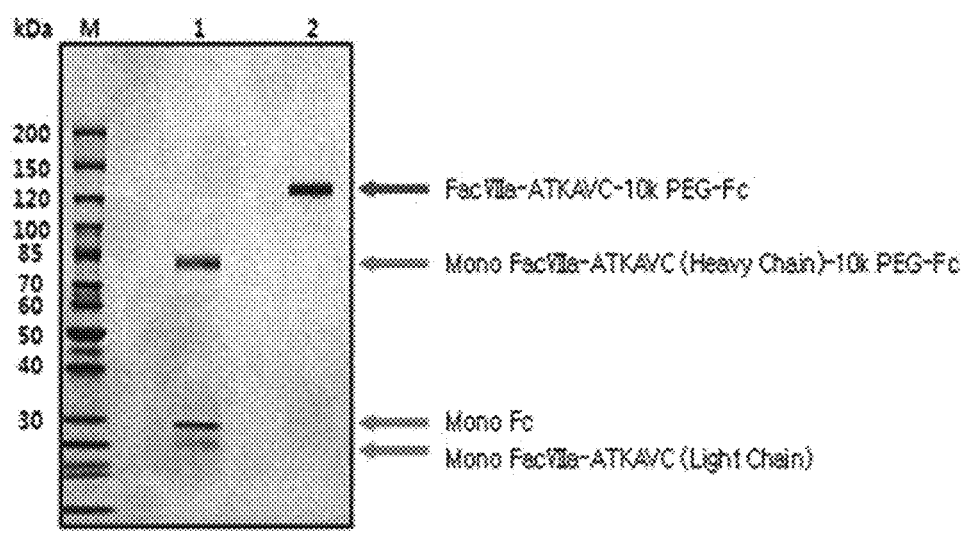
FIG. 4a is a photograph showing the result of electrophoresis of a FacVIIa-ATKAVC-PEG-Fc conjugate.
Figure 4B:
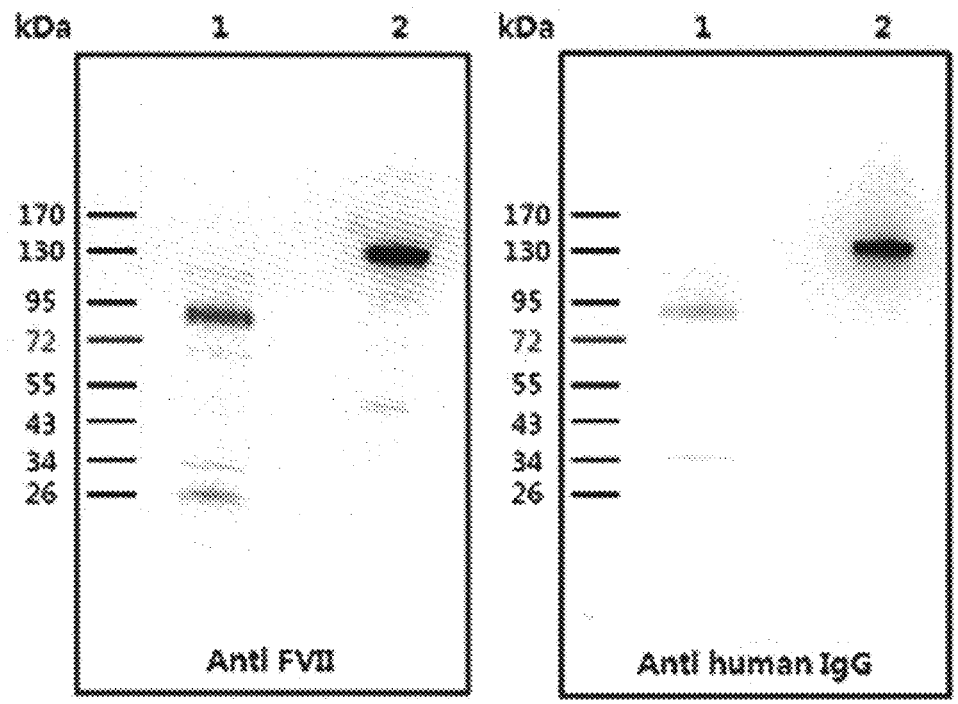
FIG. 4b is a photograph showing the result of Western blot analysis of the FacVIIa-ATKAVC-PEG-Fc conjugate.

The purity of the purified FacVII-ATKAVC-PEG-Fc was examined by SDS PAGE and Western blotting (FIG. 4). FIG. 4a is a photograph showing the result of electrophoresis of the purified FacVIIa-ATKAVC-PEG-Fc conjugate, in which M is a size marker, Lane 1 is FacVII-ATKAVC-PEG-Fc under reducing conditions, and Lane 2 is FacVIIa-ATKAVC-PEG-Fc under non-reducing conditions. FIG. 4b is a photograph showing the result of Western blot analysis of the purified FacVIIa-ATKAVC-PEG-Fc, in which Lane 1 is FacVIIa-ATKAVC-PEG-Fc under reducing conditions, and Lane 2 is FacVIIa-ATKAVC-PEG-Fc under non-reducing conditions.

Example 6

In Vitro Activity ($EC_{50}$) of FacVII and FacVII-ATKAVC

In order to determine in vitro activities of FacVII and FacVII-ATKAVC, a commercial kit (Chromogenix, COASET) was used to perform chromogenic assay. The activity assay was performed in accordance with the European Pharmacopoeia "2.7.10. ASSAY OF HUMAN COAGULATION FACTOR VII".

The diluted FacVII and FacVII-ATKAVC are activated by thromboplastin and $Ca^{2+}$ ions. FX is activated to FXa by the activated FacVIIa and FacVIIa-ATKAVC, and a substrate S-2765 (N-a-Cbo-D-Arg-Gly-Arg-pNA) is hydrolyzed and dissociated into a peptide and a chromophoric group pNA by the activated FXa. The absorbance of the dissociated pNA at 405 nm was monitored to determine the in vitro activities of FacVIIa and FacVIIa-ATKAVC.

Changes in absorbance according to the concentrations of FacVII and FacVII-ATKAVC were examined by regression analysis using a 4-parameter model of Softmax Pro 4.0 program, and the activities between two substances were compared using the obtained $EC_{50}$ values.

The test results (FIG. 5 and Table 1) showed that the in vitro activity of FacVII-ATKAVC shows a titer equivalent to or higher than that of the native FacVII.

TABLE 1

$EC_{50}$ comparison between FacVII and FacVII-ATKAVC

| | | $EC_{50}$ (ng/mL) (Relative activity, %) | |
|---|---|---|---|
| | Lot. No. | Run 1 | Run 2 |
| FacVII | B13161-PKC251 | 1.62 (100) | 1.67 (100) |
| FacVII-ATKAVC | B13090-PKI111 | 1.36 (119) | 1.16 (143) |

Figure 5:
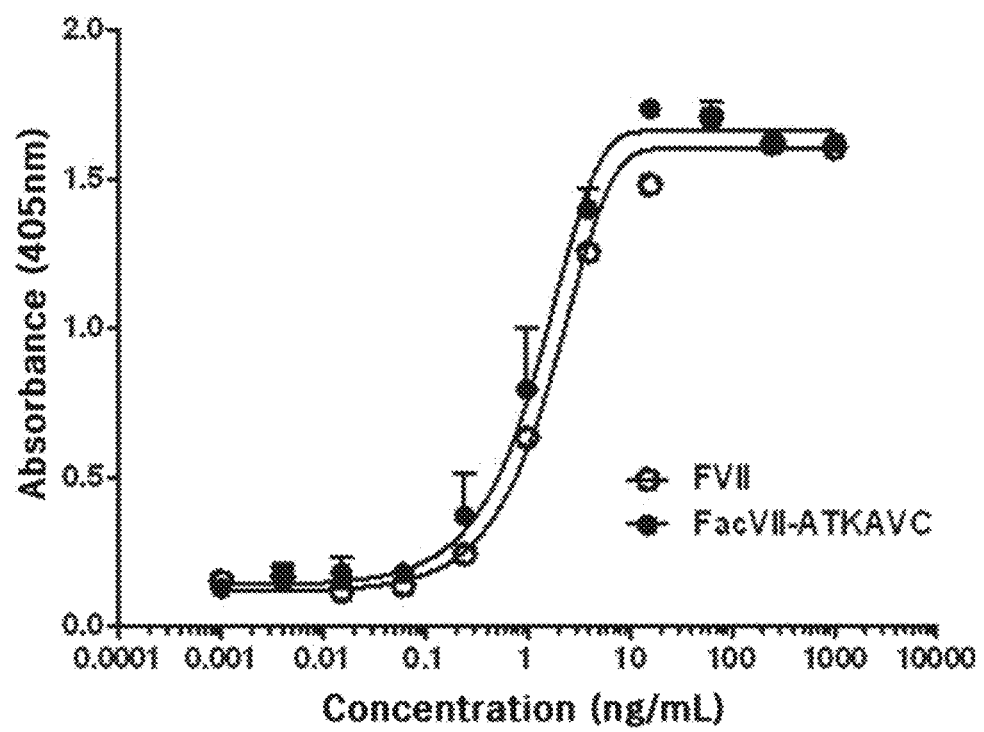
FIG. 5 is a graph of concentration-dependent absorbance showing in vitro activities of FacVII and FacVII-ATKAVC.

As shown in Table 1 and FIG. 5, FacVII and FacVII-ATKAVC were found to exhibit equivalent in vitro activities, indicating that the FacVII or FacVII derivative of the present invention has an activity equivalent to that of native form, and addition of a peptide linker to the C-terminus does not affect its activity.

Example 7

In Vitro Activity ($EC_{50}$) of FacVII-ATKAVC and FacVII-ATKAVC-40 kDa PEG

In order to examine the activity according to site-specific conjugation, in vitro activities of FacVII-40 kDa PEG, FacVII-ATKAVC, and C-terminal PEGylated FacVII-ATKAVC-40 kDa PEG were determined. A commercial kit (Chromogenix, COASET) was used to perform chromogenic assay, and the method was performed in the same manner as in Example 6. Changes in absorbance according to the concentrations of test samples were examined using a 4-parameter model of Softmax Pro 4.0 program, and the relative activities after PEGylation were examined using the obtained $EC_{50}$ values.

The test results (Table 2) showed that the in vitro activity of N-terminal PEGylated FacVII-40 kDa PEG shows a titer of approximately 11%, compared to FacVII, and in vitro activity of C-terminal PEGylated FacVII-ATKAVC-40 kDa PEG shows a titer of approximately 29%, compared to FacVII-ATKAVC.

TABLE 2

$EC_{50}$ comparison between FacVII-ATKAVC and FacVII-ATKAVC-40 kDa PEG

| | Lot. No. | $EC_{50}$ (ng/mL) (Relative activity, %) |
|---|---|---|
| FacVII | B13160-PJE261 | 1.38 (100) |
| FacVI-40 kDa PEG | B13161-PKI291 | 12.17 (11.3) |
| FacVII-ATKAVC | B13190-PKI261 | 1.75 (100) |
| FacVII-ATKAVC-40 kDa PEG | B13161-PKI292 | 6.06 (28.9) |

The activity of the conjugate of PEG and FacVII derivative of the present invention showed a titer of approximately 29%, compared to FacVII derivative. In contrast, the activity of the conjugate of PEG and FacVII showed a titer of approximately 11%, compared to FacVII. These results indicate that the C-terminal PEGylated FacVII-ATKAVC-40 kDa PEG maintains approximately 2.5 times higher relative activity, compared to $EC_{50}$ of the N-terminal PEGylated FacVII-40 kDa PEG, and the activity of FacVII can be highly maintained by site-specific conjugation using ATKAVC.

Example 8

In Vitro Activity of FacVIIa-ATKAVC-PEG-Fc

In vitro activity of FacVIIa-ATKAVC-PEG-Fc was determined using a commercial kit (StaclotVIIa-rTF, Stago) and international standard NIBSC Factor VIIa (656 IU/vial, Code No. 07/228) as a standard material. This method is based on coagulation by specific reaction of rsTF (recombinant soluble tissue factor) and Factor VIIa. NIBSC Factor VIIa, FacVIIa-ATKAVC, and FacVIIa-ATKAVC-PEG-Fc were diluted with FacVII-deficient human plasma at a ratio of 1:1, and reacted with a mixture of rsTF and phospholipid for approximately 180 seconds. Thereafter, 25 mM $CaCl_2$ was added thereto to measure the time of coagulation. As the amount of Factor VIIa increases, the coagulation time becomes shorter.

In order to calculate a specific activity (IU/mg) of FacVIIa-ATKAVC and FacVIIa-ATKAVC-PEG-Fc, potencies (IU/mL) of FacVIIa-ATKAVC and FacVIIa-ATKAVC-PEG-Fc relative to potency (IU/mL) of NIBSC Factor VIIa were first analyzed using PLA 2.0. Thereafter, the calculated potency (IU/mL) was divided by the protein concentration (mg/mL) to calculate the specific activity.

The test results (Table 3) showed that in vitro activity of FacVIIa-ATKAVC-PEG-Fc was approximately 20632 IU/mg, indicating that it maintains approximately 45% activity, compared to FacVIIa-ATKAVC.

TABLE 3

In vitro activity of FacVIIa-ATKAVC-PEG-Fc

| | Lot. No. | Potency (IU/mL) | Specific activity (IU/mg as FacVIIa) (Residual activity, %) |
|---|---|---|---|
| FacVIIa-ATKAVC | B13090-PLD111 | 16704.0 | 46143.6 (100) |
| FacVIIa-ATKAVC-PEG-Fc | B13099-LLA041 | 1993.7 | 20632.2 (44.7) |

The invention claimed is:

1. A derivative of blood coagulation factor VII (FacVII) or its active form FacVIIa, comprising the amino acid sequence of SEQ ID NO: 4 of the FacVII and a peptide linker, said peptide linker being linked to the FacVII or FacVIIa at the C-terminus of the FacVII or FacVIIa,
wherein the peptide linker consists of 6-149 consecutive amino acid residues starting from the amino acid residue at position 1 of SEQ ID NO: 30.

2. The derivative according to claim 1, wherein the amino acid residue of the C-terminus of the peptide linker is a cysteine.

3. The derivative according to claim 1, wherein the sequence of valine-leucine-lysine-glycine of SEQ ID NO: 36 at positions 7 through 10 of SEQ ID NO: 30 is replaced with the sequence of isoleucine-proline-arginine-isoleucine of SEQ ID NO: 37.

4. The derivative according to claim 1, wherein the derivative consists of one of the amino acid sequences selected from the group consisting of SEQ ID NOs: 9, 13, 14, 20, 24, 27, 34, and 35.

5. The derivative of claim 1, wherein the peptide linker is selected from the group consisting of SEQ ID NOs: 5, 31, 32, and 33.

6. A pharmaceutical composition, comprising the FacVII derivative or the FacVIIa derivative of claim 1, as an active ingredient.

7. A conjugate of blood coagulation factor VII (FacVII) or its active form FacVIIa and a non-peptidyl polymer, wherein the non-peptidyl polymer is linked to the peptide linker of the derivative of FacVII or its active form FacVIIa of claim 1, and wherein the conjugate has an extended blood half-life compared to a non-conjugated FacVII or FacVIIa.

8. The conjugate according to claim 7, wherein the non-peptidyl polymer is linked to the C-terminus of the peptide linker of the derivative of FacVII or its active form FacVIIa.

9. The conjugate according to claim 7, wherein the non-peptidyl polymer has one or more reactive group selected from the group consisting of an aldehyde group, a propionaldehyde group, a butyraldehyde group, a maleimide group, ortho pyridyl disulfide, a thiol and a succinimidyl group.

10. The conjugate according to claim 9, wherein the succinimidyl group is succinimidyl propionate, succinimidyl carboxymethyl, hydroxy succinimidyl or succinimidyl carbonate.

11. The conjugate according to claim 7, wherein the non-peptidyl polymer has two or three reactive ends.

12. The conjugate according to claim 7, wherein the non-peptidyl polymer has a maleimide reactive group or an aldehyde reactive group at both ends, respectively.

13. The conjugate according to claim 7, wherein the non-peptidyl polymer is selected from the group consisting of polyethylene glycol, polypropylene glycol, ethylene glycol-propylene glycol non-peptidyl copolymers, polyoxyethylated polyols, polyvinyl alcohols, polysaccharides, dextrans, polyvinyl ethyl ethers, biodegradable polymers, lipid non-peptidyl polymers, chitins, hyaluronic acids, and a combination thereof.

14. The conjugate according to claim 7, wherein one end of the non-peptidyl polymer constituting the FacVII conjugate or FacVIIa conjugate is further linked to a carrier selected from the group consisting of an antibody, albumin, and transferrin.

15. A pharmaceutical composition, comprising the FacVII conjugate or the FacVIIa conjugate of claim 7, as an active ingredient.

16. A complex of blood coagulation factor VII (FacVII) or its active form FacVIIa that is composed of the FacVII or FacVIIa derivative of claim 1, an immunoglobulin Fc region, and a non-peptidyl polymer, wherein the FacVII or FacVIIa derivative is linked to the immunoglobulin Fc region via the non-peptidyl polymer.

17. The complex according to claim 16, wherein the non-peptidyl polymer is selected from the group consisting of polyethylene glycol, polypropylene glycol, ethylene glycol-propylene glycol copolymers, polyoxyethylated polyols, polyvinyl alcohols, polysaccharides, dextrans, polyvinyl ethyl ethers, biodegradable polymers, lipid polymers, chitins, hyaluronic acids, and a combination thereof.

18. The complex according to claim 16, wherein the non-peptidyl polymer has one, two or three reactive ends.

19. The complex according to claim 16, wherein the non-peptidyl polymer has a maleimide reactive group or an aldehyde reactive group at both ends, respectively.

20. The complex according to claim 16, wherein the immunoglobulin Fc region is composed of one to four domains selected from the group consisting of CH1, CH2, CH3 and CH4 domains.

21. The complex according to claim 16, wherein the immunoglobulin Fc region further comprises a hinge region.

22. The complex according to claim 16, wherein the immunoglobulin Fc region is derived from IgG, IgA, IgD, IgE, or IgM.

23. The complex according to claim 16, wherein the immunoglobulin Fc region is an IgG4 Fc region.

24. The complex according to claim 16, wherein the immunoglobulin Fc region is a human aglycosylated IgG4 Fc region.

25. A pharmaceutical composition, comprising the FacVII complex or the FacVIIa complex of claim 16, as an active ingredient.

26. A method for treating hemophilia, comprising the step of administering to a subject in need thereof a therapeutically effective amount of the pharmaceutical composition of claim 6.

27. A method for promoting blood coagulation, comprising the step of administering to a subject in need thereof a therapeutically effective amount of the pharmaceutical composition claim 6.

* * * * *